(12) United States Patent
Collingwood et al.

(10) Patent No.: US 6,589,950 B1
(45) Date of Patent: Jul. 8, 2003

(54) PURINE DERIVATIVES INHIBITORS OF TYROSINE PROTEIN KINASE SYK

(75) Inventors: Stephen Paul Collingwood, Horsham (GB); Judy Hayler, Horsham (GB); Darren Mark Le Grand, Horsham (GB); Henri Mattes, Brunstatt (FR); Keith Allan Menear, Horsham (GB); Clive Victor Walker, Horsham (GB); Xiao-Ling Cockcroft, Horsham (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/048,577

(22) PCT Filed: Jul. 28, 2000

(86) PCT No.: PCT/EP00/07311

§ 371 (c)(1),
(2), (4) Date: Mar. 19, 2002

(87) PCT Pub. No.: WO01/09134

PCT Pub. Date: Feb. 8, 2001

(30) Foreign Application Priority Data

Jul. 30, 1999 (GB) .............................. 9918035

(51) Int. Cl.⁷ .................. C07D 473/16; C07D 473/18; C07D 473/24; A61K 31/52; A61K 31/522
(52) U.S. Cl. ........................ 514/234.2; 514/263.37; 514/263.4; 544/118; 544/276; 544/277
(58) Field of Search ................. 514/234.2, 263.37; 544/276, 277, 118

(56) References Cited

U.S. PATENT DOCUMENTS

| | | | |
|---|---|---|---|
| 4,853,386 A | 8/1989 | Friebe et al. | |
| 2002/0016329 A1 * | 2/2002 | Imbach et al. | 544/277 |

FOREIGN PATENT DOCUMENTS

| | | |
|---|---|---|
| EP | 0 212 535 | 3/1987 |
| WO | WO 93/17021 | 9/1993 |
| WO | WO 93/20078 | 10/1993 |
| WO | WO 95/35304 | 12/1995 |
| WO | WO 9716452 A1 * 5/1997 | ......... C07D/473/16 |
| WO | WO 98/05335 | 2/1998 |
| WO | WO 99/07705 | 2/1999 |

OTHER PUBLICATIONS

Dorland's Illustrated Medical Dictionary, 28ᵗʰ Edition (Saunder Company) p. 1385.*
Benjamin K. Gill, "Diagram Representing the Roles of Cytokines in Inflammatory Responses" http://attila.stevens-tech.edu/chembio/bgill/IL10K.html.*
Talanian, Robert et al., Mol. Aspects Chemother., Proc. Int. Symp., 2ⁿᵈ, pp. 105–118 (1990).
Wright, George E. et al., J. Med. Chem., vol. 30, No. 1, pp. 109–116 (1987).
Matselyukh, B.P. et al., Chem. Abst. 81:163864 (1974).
Tret'yakova, G.S. et al., Chem. Abst. 78:16123 (1972).

* cited by examiner

*Primary Examiner*—Mark L. Berch
(74) *Attorney, Agent, or Firm*—Gabriel Lopez; George R. Dohmann

(57) ABSTRACT

Disclosed are compounds of the formula

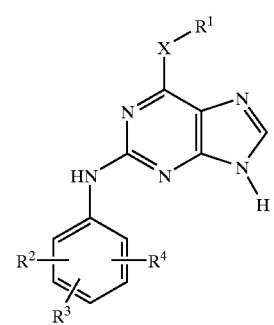

in free or salt form, wherein X, $R^1$, $R^2$, $R^3$, and $R^4$ are as defined in the specification, their preparation and their use as pharmaceuticals, particularly for the treatment of inflammatory or obstructive airways disease.

12 Claims, No Drawings

PURINE DERIVATIVES INHIBITORS OF TYROSINE PROTEIN KINASE SYK

This invention relates; to organic compounds, their preparation and their use as pharmaceuticals.

More particularly, the present invention relates to:
(a) compounds of formula

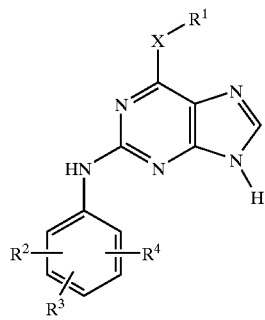

in free or salt form, where
X is an oxygen or sulfur atom or a group $NR^5$,
$R^1$ is an alkyl, alkenyl, cycloalkyl, benzocycloalkyl, cycloalkylalkyl or aralkyl group which optionally may be substituted by hydroxy, alkoxy, carboxy or alkoxycarbonyl or, when X is $NR^5$, $R^1$ may alternatively be a heterocyclyl group or a group of formula

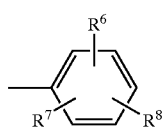

$R^2$, $R^3$, $R^4$, $R^6$, $R^7$ and $R^8$ are each independently hydrogen, halogen, alkyl, haloalkyl, alkoxy, carboxy, alkoxycarbonyl, carboxyalkyl, alkoxycarbonylalkyl, —$N(R^9)R^{10}$, —$SO_2N(R^{11})R^{12}$, $C_1$-$C_4$-alkylene-$SO_2N(R^{11})R^{12}$ or —$CON(R^{13})R^{14}$ or, when two of $R^2$, $R^3$ and $R^4$, or two of $R^6$, $R^7$ and $R^8$, are attached to adjacent carbon atoms on the indicated benzene rings, they denote, together with the carbon atoms to which they are attached, a carbocyclic group having 5 to 10 ring atoms or a heterocyclic group having 5 to 10 ring atoms of which one, two or three are hetero atoms selected from nitrogen, oxygen and
$R^5$ is hydrogen or alkyl,
$R^9$ is hydrogen or alkyl and $R^{10}$ is hydrogen, alkyl or —$COR^{15}$ where $R^{15}$ is alkyl, haloalkyl, alkoxy, alkoxyalkyl, alkoxycarbonyl, carboxyalkyl or alkoxycarbonylalkyl, or $R^9$ and $R^{10}$, together with the nitrogen atom to which they are attached, denote a heterocyclic group having 5 or 6 ring atoms of which one or two are hetero atoms selected from nitrogen, oxygen and sulfur,
$R^{11}$ is hydrogen or alkyl and $R^{12}$ is hydrogen, alkyl, hydroxyalkyl, alkoxyalkyl, carboxyalkyl or alkoxycarbonylalkyl, or $R^{11}$ and $R^{12}$ together with the nitrogen atom to which they are attached denote a heterocyclic group having 5 or 6 ring atoms of which one or two are hetero atoms selected from nitrogen, oxygen and sulfur, and
$R^{13}$ and $R^{14}$ are each independently hydrogen or alkyl; particularly to compounds of formula I in free or pharmaceutically acceptable salt form for use as pharmaceuticals; and (b) compounds of formula I as hereinbefore defined in free or pharmaceutically acceptable salt form for use in the manufacture of medicaments for the treatment of conditions mediated by syk kinase.

In formula I, $R^9$, $R^{10}$, $R^{11}$, $R^{12}$, $R^{13}$ or $R^{14}$ in $R^2$, $R^3$ or $R^4$ may be the same as, or may differ from, the respective group in $R^6$, $R^7$ or $R^8$.

In another aspect, the present invention provides compounds of formula I as hereinbefore defined in free or salt form, with the exception of 2-(p-n-butylanilino)-6-methoxypurine, 2-(p-n-butylanilino)-6-(methylthio)purine, 2,6-di(phenylamino)purine, 2,6-di(p-tolylamino)purine, and 2-(p-tolylamino)-6-(phenylamino)purine.

In a further aspect, the present invention provides compounds of formula I as hereinbefore defined in free or salt form, with the exception of compounds of formula I where (i) X is oxygen or sulfur, $R^1$ is alkyl, two of $R^2$, $R^3$ and $R^4$ are hydrogen and one of $R^2$, $R^3$ and $R^4$ is alkyl and (ii) X is NH, $R^1$ is a group of formula II in which two of $R^6$, $R^7$ and $R^8$ are hydrogen and the remaining one is hydrogen or alkyl, one of $R^2$, $R^3$, and $R^4$ is hydrogen and the remaining two are each hydrogen or alkyl.

In a further aspect, the present invention provides a compound of formula I as hereinbefore described in free or salt form in which (a) X is $NR^5$ and $R^1$, $R^2$, $R^3$, $R^4$ and $R^5$ are as hereinbefore defined, with the proviso that when $R^1$ is a group of formula II, $R^6$, $R^7$ and $R^8$ are each independently halogen, haloalkyl, alkoxy, carboxy, alkoxycarbonyl, carboxyalkyl, alkoxycarbonylalkyl, —$N(R^9)R^{10}$, —$SO_2N(R^{11})R^{12}$, $C_1$-$C_4$-alkylene-$SO_2N(R^{11})R^{12}$ or —$CON(R^{13})R^{14}$ or, when two of $R^6$, $R^7$ and $R^8$ are attached to adjacent carbon atoms on the indicated benzene ring, they denote, together with the carbon atoms to which they are attached, a carbocyclic group having 5 to 10 ring atoms or a heterocyclic group having 5 to 10 ring atoms of which one, two or three are hetero atoms selected from nitrogen, oxygen and sulfur, or one or two of $R^6$, $R^7$ and $R^8$ are hydrogen; or (b) X is oxygen or sulfur and $R^1$, $R^2$, $R^3$ and $R^4$ are as hereinbefore defined, with the proviso that when $R^1$ is alkyl, $R^2$, $R^3$ and $R^4$ are each independently hydrogen, halogen, alkoxy, carboxy, alkoxycarbonyl, carboxyalkyl, alkoxycarbonylalkyl, —$N(R^9)R^{10}$, —$SO_2N(R^{11})R^{12}$, $C_1$-$C_4$-alkylene-$SO_2N(R^{11})R^{12}$ or —$CON(R^{13})R^{14}$ or, when two of $R^2$, $R^3$ and $R^4$ are attached to adjacent carbon atoms on the indicated benzene rings, they denote, together with the carbon atoms to which they are attached, a carbocyclic group having 5 to 10 ring atoms or a heterocyclic group having 5 to 10 ring atoms of which one, two or three are hetero atoms selected from nitrogen, oxygen and sulfur.

Terms used in this specification have the following meanings:

"Alkyl" denotes straight chain or branched alkyl, which may be, for example, $C_1$ to $C_{10}$-alkyl such as methyl, ethyl, n-propyl, isopropyl, n-butyl, isobutyl, sec-butyl, tert-butyl, straight or branched pentyl, straight or branched hexyl, straight or branched heptyl, straight or branched nonyl or straight or branched decyl. Preferably alkyl is $C_1$ to $C_4$-alkyl.

"Alkoxy" denotes straight chain or branched alkoxy and may be, for example, $C_1$ to $C_{10}$ alkoxy such as methoxy, ethoxy, n-propoxy, isopropoxy, n-butoxy, isobutoxy, sec-butoxy, tert-butoxy, or straight or branched pentoxy, hexyloxy, heptyloxy, octyloxy, nonyloxy or decyloxy. Preferably alkoxy is $C_1$ to $C_4$-alkoxy.

"Alkenyl" means straight chain or branched alkenyl, which may be, for example, $C_2$ to $C_{10}$-alkenyl such as vinyl, 1-propenyl, 2-propenyl, 1-butenyl, isobutenyl, or straight or branched pentenyl, hexenyl, heptenyl, octenyl, nonenyl or decenyl. Preferred alkenyl is $C_2$ to $C_4$-alkenyl.

"Cycloalkyl" means $C_3$ to $C_{10}$-cycloalkyl having 3 to 8 ring carbon atoms and may be, for example, cyclopropyl, cyclobutyl, cyclopentyl, cyclohexyl, cycloheptyl or cycloheptyl, any of which can be substituted by one, two or more $C_1$–$C_4$ alkyl groups, particularly methyl groups. Preferably, cycloalkyl is $C_3$–$C_6$-cycloalkyl.

"Benzocycloalkyl" means cycloalkyl, e.g. one of the $C_3$ to $C_{10}$ cycloalkyl groups mentioned hereinbefore, attached at two adjacent carbon atoms to a benzene ring. Preferably, benzocycloalkyl is benzo-$C_5$–$C_6$-cycloalkyl, especially benzocyclohexyl (tetrahydronaphthyl).

"Cycloalkylalkyl" means $C_3$ to $C_{10}$-cycloalkyl —$C_1$–$C_{10}$ alkyl where the $C_3$ to $C_{10}$-cycloalkyl group has 3 to 8 ring carbon atoms and may be, for example, one of the $C_1$–$C_{10}$-alkyl groups mentioned hereinbefore, particularly one of the $C_1$–$C_4$-alkyl groups, substituted by one of the $C_3$–$C_{10}$-cycloalkyl groups mentioned hereinbefore. Preferably cycloalkylalkyl is $C_3$–$C_6$-cycloalkyl-$C_1$–$C_4$-alkyl.

"Aralkyl" means $C_6$–$C_{10}$-aryl-$C_1$–$C_{10}$ alkyl and may be, for example, one of the $C_1$–$C_{10}$-alkyl groups mentioned hereinbefore, particularly one of the $C_1$–$C_4$-alkyl groups, substituted by phenyl, tolyl, xylyl or naphthyl. Preferably, aralkyl is phenyl-$C_1$–$C_4$-alkyl, particularly benzyl or 2-phenylethyl.

"Heterocyclyl" means a monovalent heterocyclic radical having up to 20 carbon atoms and one, two, three or four heteroatoms selected from nitrogen, oxygen and sulfur, the radical optionally having an alkyl, alkylcarbonyl, hydroxyalkyl, alkoxyalkyl or aralkyl group attached to a ring carbon or nitrogen atom and being linked to the remainder of the molecule through a ring carbon atom, and may be, for example, a radical, preferably a monocyclic radical, with one nitrogen, oxygen or sulfur atom such as pyrryl, pyridyl, piperidyl, furyl, tetrahydrofuryl or thienyl, or a radical, preferably a monocyclic radical, with two hetero atoms selected from nitrogen, oxygen and sulfur, such as imidazolyl, pyrimidinyl, piperazinyl, oxazolyl, isoxazolyl, thiazolyl, morpholinyl or thiomorpholinyl. Preferably, heterocyclyl is a monocyclic radical having 5 or 6 ring atoms and one or two nitrogen atoms, or one nitrogen atom and one oxygen atom, in the ring and optionally substituted on a ring nitrogen atom by $C_1$–$C_4$-alkyl, hydroxy-$C_1$–$C_4$-alkyl, $C_1$–$C_4$-alkylcarbonyl or phenyl-$C_1$–$C_4$-alkyl.

"Alkoxyalkyl" means straight chain or branched alkyl substituted by one or more alkoxy groups and may be, for example, a $C_1$–$C_{10}$-alkoxy-$C_1$–$C_{10}$-alkyl group, such as one of the $C_1$–$C_{10}$-alkyl groups, particularly one of the $C_1$–$C_4$-alkyl groups, mentioned hereinbefore substituted by one of the $C_1$–$C_{10}$-alkoxy groups, preferably one of the $C_1$–$C_4$-alkoxy groups, mentioned hereinbefore. Preferably alkoxyalkyl is $C_1$–$C_4$-alkoxy-$C_1$–$C_4$ alkyl.

"Carboxyalkyl" means straight chain or branched alkyl, for example $C_1$–$C_{10}$-alkyl such as one of the $C_1$–$C_{10}$-alkyl groups mentioned hereinbefore, substituted, preferably on a primary carbon atom, by a carboxyl group. Preferably carboxyalkyl is carboxy-$C_1$–$C_4$-alkyl.

"Alkylcarbonyl" means a group $R^{16}CO$ where $R^{16}$ is alkyl, for example $C_1$–$C_{10}$-alkyl such as one of the $C_1$–$C_{10}$-, preferably $C_1$–$C_4$-, alkyl groups mentioned hereinbefore.

Preferably, alkylcarbonyl is $C_1$–$C_4$-alkylcarbonyl, i.e. $R^{16}CO$ where $R^{16}$ is $C_1$–$C_4$-alkyl.

"Alkoxycarbonyl" means a group $R^{17}CO$ where $R^{17}$ is an alkoxy group, for example a $C_1$–$C_{10}$ alkoxy group such as one of the $C_1$–$C_{10}$, preferably $C_1$–$C_4$, alkoxy groups mentioned hereinbefore. Preferably, alkoxycarbonyl is $C_1$–$C_4$-alkoxycarbonyl, i.e. $R^{17}CO$ where $R^{17}$ is $C_1$–$C_4$-alkoxy.

"Alkoxycarbonylalkyl" means straight or branched chain alkyl, for example a $C_1$–$C_{10}$ alkyl group such as one of the $C_1$–$C_{10}$-, preferably $C_1$–$C_4$-, alkyl groups mentioned hereinbefore, substituted by an alkoxycarbonyl group as hereinbefore defined. Preferably, alkoxycarbonylalkyl is $C_1$–$C_4$-alkoxy-carbonyl-$C_1$–$C_4$-alkyl.

"Haloalkyl" means straight chain or branched alkyl, for example $C_1$–$C_{10}$-alkyl such as one of the $C_1$–$C_{10}$-alkyl groups mentioned hereinbefore, substituted by one or more, for example one, two or three, halogen atoms, preferably fluorine or chlorine atoms. Preferably haloalkyl is $C_1$–$C_4$-alkyl substituted by one, two or three fluorine or chlorine atoms.

"Hydroxyalkyl" means straight chain or branched alkyl, for example $C_1$–$C_{10}$-alkyl such as one of the $C_1$–$C_{10}$-alkyl groups mentioned hereinbefore, substituted by one, two or three hydroxyl groups. Preferably, hydroxyalkyl is $C_1$–$C_4$-alkyl substituted by one hydroxyl group.

Where one of $R^2$, $R^3$ and $R^4$, or one of $R^6$, $R^7$ and $R^8$, is hydrogen and the second and third of $R^2$, $R^3$ and $R^4$, or the second and third of $R^6$, $R^7$ and $R^8$, are attached to adjacent carbon atoms in the respective benzene ring and together with said adjacent carbon atoms denote a carbocyclic group or heterocyclic group, the second and third of $R^2$, $R^3$ and $R^4$, or the second and third of $R^6$, $R^7$ and $R^8$, may denote, together with the benzene ring to which they are attached, a $C_9$–$C_{15}$-carbocyclic group such as indenyl or naphthyl, optionally substituted by one or more $C_1$–$C_4$-alkyl or $C_1$–$C_4$-alkoxy groups, dihydronaphthyl, tetrahydronaphthyl, fluorenyl, anthryl or phenanthryl, preferably a $C_{10}$–$C_{15}$-carbocyclic aromatic group or tetrahydronaphthyl; or the second and third of $R^2$, $R^3$ and $R^4$, or the second and third of $R^6$, $R^7$ and $R^8$, may denote, together with the benzene ring to which they are attached, a heterocyclic group having 9 to 14 ring atoms, of which one, two or three are heteroatoms selected from nitrogen, oxygen and sulfur, for example an indolyl, benzimidazolyl, indazolyl or carbazolyl group (which is optionally substituted on a nitrogen atom by $C_1$–$C_4$-alkyl, hydroxy-$C_1$–$C_4$-alkyl or phenyl-$C_1$–$C_4$-alkyl), or benzofuranyl, benzothiophenyl, qunolinyl, isoquinolinyl, naphthyridinyl, dioxanapthyl (benzodioxanyl), benzoxazolyl, benzothiazolyl, benzofuranonyl or benzofurazanyl, preferably a heterocyclic group having 9 to 13 ring atoms, of which one or two are hetero atoms selected from nitrogen, oxygen and sulfur.

Where $R^9$ and $R^{10}$, or $R^{11}$ and $R_{12}$, together with the nitrogen atom to which they are attached, denote a heterocyclic group, the heterocyclic group may be, for example, a group having one or two nitrogen atoms in the ring such as a pyrrolidinyl, imidazolyl, imidazolidinyl, piperidyl or piperazinyl group, the group having two nitrogen atoms in the ring being optionally substituted on the second nitrogen atom by a $C_1$–$C_4$-alkyl, hydroxy-$C_1$–$C_4$-alkyl, $C_1$–$C_4$-alkylcarbonyl, a $C_1$–$C_4$-alkoxycarbonyl or phenyl-$C_1$–$C_4$-alkyl group, or the heterocyclic group may be a group having one nitrogen atom and one oxygen atom in the ring, such as a tetrahydro-oxazolyl, tetrahydro-isoxazolyl or mopholino group, which may be substituted on one or more ring carbon atoms by a $C_1$–$C_4$-alkyl group.

Preferred compounds of formula I and their salts are compounds of formula

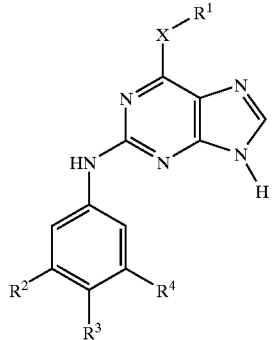

III in free or salt form, where
$R^1$ is as hereinbefore and, when it is a group of formula II, it is a group of formula

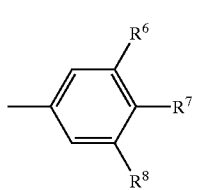

IV and $R^2$, $R^3$, $R^4$, $R^6$, $R^7$ and $R^8$ are as hereinbefore defined.

Preferably, in formula I and formula III, $R^1$ is a $C_1$–$C_{10}$-alkyl, especially $C_1$–$C_4$-alkyl, $C_2$–$C_{10}$-alkenyl, especially $C_2$–$C_4$-alkenyl, $C_3$–$C_{10}$-cycloalkyl, especially $C_3$–$C_6$-cycloalkyl, benz-$C_3$–$C_{10}$-cycloalkyl, especially benzo-$C_5$–$C_6$-cycloalkyl, phenyl-$C_1$–$C_{10}$-alkyl, especially phenyl-$C_1$–$C_4$-alkyl, or $C_3$–$C_{10}$-cycloalkyl-$C_1$–$C_4$-alkyl, especially $C_3$–$C_6$-cycloalkyl-$C_1$–$C_4$-alkyl, group which is optionally substituted by a hydroxy, carboxy or $C_1$–$C_4$-alkoxycarbonyl group, or $R^1$ is a heterocyclyl radical having 5 or 6 ring atoms and one or two nitrogen atoms, or one nitrogen atom and one oxygen atom, in the ring and optionally substituted on a ring nitrogen atom by $C_1$–$C_4$-alkyl, hydroxy-$C_1$–$C_4$-alkyl, $C_1$–$C_4$-alkylcarbonyl or phenyl-$C_1$–$C_4$-alkyl, or $R^1$ is a group of formula II or formula IV respectively in which one of $R^6$, $R^7$ and $R^8$ is hydrogen, $C_1$–$C_4$-alkyl or $C_1$–$C_4$-alkoxy, and (i) the second and third of $R^6$, $R^7$ and $R^8$ are each independently hydrogen, $C_1$–$C_4$-alkyl or $C_1$–$C_4$-alkoxy or (ii) the second of $R^6$, $R^7$ and $R^8$ is hydrogen and the third of $R^6$, $R^7$ and $R^8$ is carboxy, $C_1$–$C_{10}$-, preferably $C_1$–$C_4$-alkoxycarbonyl, carboxy $C_1$–$C_{10}$-, preferably carboxy-$C_1$–$C_4$-alkyl, $C_1$–$C_{10}$-alkoxycarbonyl-$C_1$–$C_{10}$-alkyl, preferably $C_1$–$C_4$-alkoxycarbonyl-$C_1$–$C_4$-alkyl, —N($R^9$)$R^{10}$, —SO$_2$N ($R^{11}$)$R^{12}$, $C_1$–$C_4$-alkylene-SO$_2$N($R^{11}$)$R^{12}$ or —CON ($R^{13}$)$R^{14}$, or (iii) the second and third of $R^6$, $R^7$ and $R^8$ are attached to adjacent carbon atoms in the indicated benzene ring and, together with said adjacent carbon atoms, denote a carbocyclic group having 5 or 6 ring atoms or a monocyclic heterocyclic group having 5 or 6 ring atoms and one or two nitrogen atoms in the ring, one of $R^2$, $R^3$ and $R^4$ is hydrogen, $C_1$–$C_4$-alkyl or $C_1$–$C_4$-alkoxy and (a) the second and third of $R^2$, $R^3$ and $R^4$ are each independently hydrogen, $C_1$–$C_4$-alkyl or $C_1$–$C_4$-alkoxy, or (b) the second of $R^2$, $R^3$ and $R^4$ is hydrogen and the third of $R^2$, $R^3$ and $R^4$ is carboxy, $C_1$ . $C_{10}$,
preferably $C_1$–$C_4$-, alkoxycarbonyl, carboxy-$C_1$–$C_{10}$-oalkyl, preferably carboxy-$C_1$–$C_4$-alkyl, $C_1$–$C_{10}$-alkoxycarbonyl-$C_1$–$C_{10}$-alkyl, preferably $C_1$–$C_4$-alkoxycarbonyl-$C_1$–$C_4$-alkyl, —N($R^9$)$R^{10}$, —SO$_2$N ($R^{11}$)$R^{12}$, $C_1$–$C_4$-alkylene-SO$_2$N($R^{11}$)$R^{12}$ or —CON ($R^{13}$)$R^4$, or (c) the second and third of $R^2$, $R^3$ and $R^4$ are attached to adjacent carbon atoms in the indicated benzene ring and, together with said adjacent carbon atoms, denote a carbocyclic group having 5 or 6 ring atoms or a heterocyclic group having 5 to 10 ring atoms, of which one or two are hetero atoms selected from nitrogen, oxygen and sulfur, $R^9$ is hydrogen or $C_1$–$C_{10}$-, preferably $C_1$–$C_4$-, alkyl and $R^{10}$ is hydrogen, $C_1$–$C_{10}$-, preferably $C_1$–$C_4$-, alkyl, or —COR$^{15}$ where $R^{15}$ is $C_1$–$C_{10}$-, preferably $C_1$–$C_4$-, alkyl, $C_1$–$C_{10}$-haloalkyl, preferably $C_1$–$C_4$-haloalkyl, $C_1$–$C_{10}$-alkoxy-$C_1$–$C_{10}$-alkyl, preferably $C_1$–$C_4$-alkoxy- $C_1$–$C_4$-alkyl, $C_1$–$C_{10}$-alkoxycarbonyl, preferably $C_1$–$C_4$-alkoxycarbonyl, carboxy-$C_1$–$C_{10}$-alkyl, preferably carboxy-$C_1$–$C_4$-alkyl, or $C_1$–$C_{10}$-alkoxycarbonyl-$C_1$–$C_{10}$ alkyl, preferably $C_1$–$C_4$-alkoxycarbonyl-$C_1$–$C_4$-alkyl, or $R^9$ and $R_{10}$ together with the nitrogen atom to which they are attached, denote a heterocyclic group having 5 or 6 ring atoms and one or two nitrogen atoms, or one nitrogen atom and one oxygen atom, in the ring, $R^{11}$ is hydrogen or $C_1$–$C_{10}$-, preferably $C_1$–$C_4$-, alkyl and $R^{12}$ is hydrogen, $C_1$–$C_{10}$-, preferably $C_1$–$C_4$-, alkyl, hydroxy-$C_1$–$C_{10}$-alkyl, preferably hydroxy-$C_1$–$C_4$-alkyl, $C_1$–$C_{10}$-alkoxy-$C_1$–$C_{10}$-alkyl, preferably $C_1$–$C_4$-alkoxy-$C_1$–$C_4$-alkyl, carboxy-$C_1$–$C_{10}$-alkyl, preferably carboxy-$C_1$–$C_4$-alkyl, or $C_1$–$C_{10}$-alkoxycarbonyl-$C_1$–$C_{10}$-alkyl, preferably $C_1$–$C_4$-alkoxycarbonyl-$C_1$–$C_4$-alkyl, or $R^{11}$ and $R^{12}$ together with the nitrogen atom to which they are attached denote a heterocyclic group having 5 or 6 ring atoms and one or two nitrogen atoms, or one nitrogen atom and one oxygen atom, in the ring, and $R^{13}$ and $R^{14}$ are each independently hydrogen or $C_1$–$C_{10}$-, preferably $C_1$–$C_4$-, alkyl.

Preferred compounds of formula I or III and their salts include those in which:

X is a group NR$^5$, $R^1$ is a $C_1$–$C_4$-alkyl, $C_2$–$C_4$-alkenyl, $C_3$–$C_5$ cycloalkyl, benzo-$C_5$–$C_6$-cycloalkyl, phenyl-$C_1$–$C_4$-alkyl or $C_3C_5$ cycloalkyl-$C_1$–$C_4$-alkyl group, which is optionally substituted by a hydroxy, carboxy or $C_1$–$C_4$-alkoxycarbonyl group, or $R^1$ is a heterocyclyl radical having 5 or 6 ring atoms and one or two nitrogen atoms, or one nitrogen atom and one oxygen atom, in the ring and optionally substituted on a ring nitrogen atom by $C_1$–$C_4$ alkyl, $C_1$–$C_4$-hydroxyalkyl, $C_1$–$C_4$-alkylcarbonyl or phenyl-$C_1$–$C_4$-alkyl, or $R^1$ is a group of formula IV in which one of $R^6$, $R^7$ and $R^8$ is hydrogen, $C_1$–$C_4$-alkyl or alkoxy, and (i) the second and third of $R^6$, $R^7$ and $R_8$ are each independently hydrogen, $C_1$–$C_4$-alkyl or $C_1$–$C_4$-alkoxy or (ii) the second of $R^6$, $R^7$ and $R^8$ is hydrogen and the third of $R^6$, $R^7$ and $R^8$ is —N($R^9$)$R^{10}$, —SO$_2$N($R^{11}$)$R^{12}$ or —CON ($R^{13}$)$R^{14}$, or (iii) the second and third of $R^6$, $R^7$ and $R^8$ are attached to adjacent carbon atoms in the indicated benzene ring and together with said adjacent carbon atoms denote a carbocyclic group having 5 or 6 ring atoms or a heterocyclic group having 5 or 6 ring atoms, of which one or two are nitrogen atoms, one of $R^2$, $R^3$ and $R^4$ is hydrogen, $C_1$–$C_4$-alkyl or $C_1$–$C_4$-alkoxy and (a) the second and third of $R^2$, $R^3$ and $R^4$ are each independently hydrogen, $C_1$–$C_4$-alkyl or $C_1$–$C_4$-alkoxy or (b) the second of $R^2$, $R^3$ and $R^4$ is hydrogen and the third of $R^2$, $R^3$ and $R^4$ is carboxy, $C_1$–$C_4$-alkoxycarbonyl, carboxy-$C_1$–$C_4$-alkyl, $C_1$–$C_4$-alkoxycarbonyl-$C_1$–$C_4$-alkyl, —N($R^9$)$R^{10}$, —SO$_2$N($R^{11}$)$R^{12}$, $C_1$–$C_4$-alkylene-SO$_2$N($R^{11}$)$R^{12}$ or —CON($R^{13}$)$R^{14}$, or (c) the second and third of $R^2$, $R^3$ and $R^4$ are attached to adjacent carbon atoms in the indicated benzene ring and denote, together with said adjacent carbon atoms, a heterocyclic group having 5 to 10 ring atoms, of which one or two are hetero atoms selected from nitrogen, oxygen and sulfur, $R^5$ is hydrogen or $C_1$–$C_4$-alkyl, $R^9$ is hydrogen or $C_1$–$C_4$ alkyl and $R^{10}$ is hydrogen, $C_1$–$C_4$ alkyl, or —COR$^{15}$ where $R^{15}$ is $C_1$–$C_4$-alkyl, $C_1$–$C_4$-haloalkyl, $C_1$–$C_4$-alkoxy, $C_1$–$C_4$-alkoxy-$C_1$–$C_4$ alkyl, $C_1$–$C_4$-alkoxycarbonyl, or $C_1$–$C_4$-alkoxycarbonyl-$C_1$–$C_4$-alkyl, or $R^9$ and $R^{10}$ together with the nitrogen atom to which they are attached denote a heterocyclic group having 5 or 6 ring atoms including one or two ring nitrogen atoms, or one nitrogen ring atom and one oxygen ring atom, $R^{11}$ is hydrogen or $C_1$–$C_4$-alkyl and $R^{12}$ is hydrogen, $C_1$–$C_4$-alkyl, hydroxy-$C_1$–$C_4$-alkyl, $C_1$–$C_4$-alkoxy-$C_1$–$C_4$-alkyl or $C_1$–$C_4$-alkoxycarbonyl-$C_1$–$C_4$-alkyl, or $R^{11}$ and $R^{12}$ together with the nitrogen atom to which they are attached denote a heterocyclic group having 5 or 6 ring atoms including one or two ring nitrogen atoms, or one nitrogen ring atom and one oxygen ring atom, and $R^{13}$ and $R^{14}$ are each independently hydrogen or $C_1$–$C_4$-alkyl.

Further preferred amongst the above mentioned compounds where X is a group $NR^5$ are those where $R^1$ is $C_1$–$C_4$-alkyl which is optionally substituted by hydroxy, $C_2$–$C_4$-alkenyl, $C_3$–$C_5$-cycloalkyl which is optionally substituted by carboxy or $C_1$–$C_4$-alkoxycarbonyl, benzo-$C_5$–$C_6$-cycloalkyl, phenyl-$C_1$–$C_4$-alkyl optionally substituted by hydroxy, $C_3$–$C_5$-cycloalkyl-$C_1$–$C_4$-alkyl, a heterocyclyl radical having 6 ring atoms and one or two nitrogen atoms in the ring optionally substituted on a ring nitrogen atom by phenyl-$C_1$–$C_4$-alkyl, or a group of formula IV in which one of $R^6$, $R^7$ and $R^8$ is hydrogen, $C_1$–$C_4$-alkyl or $C_1$–$C_4$-alkoxy, and (i) the second and third of $R^6$, $R^7$ and $R^8$ are each hydrogen or (ii) the second of $R^6$, $R^7$ and $R^8$ is hydrogen and the third of $R^6$, $R^7$ and $R^8$ is —N($R^9$)$R^{10}$ where $R^9$ is hydrogen or $C_1$–$C_4$-alkyl and $R_{10}$ is —COR$^{15}$ where $R^{15}$ is $C_1$–$C_4$-alkyl, $C_1$–$C_4$-alkoxy, —SO$_2$N($R^{11}$)$R^{12}$ where $R^{11}$ and $R^{12}$ are each hydrogen, $C_1$–$C_4$-alkyl, or —CON($R^{13}$)$R^{14}$ where $R^{13}$ and $R^{14}$ are each hydrogen, or (iii) the second and third of $R^6$, $R^7$ and $R^8$ are attached to adjacent carbon atoms in the indicated benzene ring and denote, together with said adjacent carbon atoms, a carbocyclic group having 6 ring atoms or a heterocyclic group having 5 ring atoms, of which two are nitrogen atoms, one of $R^2$, $R^3$ and $R^4$ is hydrogen, $C_1$–$C_4$-alkyl or $C_1$–$C_4$-alkoxy, and (a) the second and third of $R^2$, $R^3$ and $R^4$ are each independently hydrogen or $C_1$–$C_4$-alkoxy or (b) the second of $R^2$, $R^3$ and $R^4$ is hydrogen and the third of $R^2$, $R^3$ and $R^4$ is carboxy, $C_1$–$C_4$-alkoxycarbonyl, carboxy-$C_1$–$C_4$-alkyl, $C_1$–$C_4$-alkoxycarbonyl-$C_1$–$C_4$-alkyl, —N($R^9$)$R^{10}$ where $R^9$ is hydrogen or $C_1$–$C_4$-alkyl and $R^{10}$ is hydrogen, $C_1$–$C_4$-alkyl, or —COR$^{15}$ where $R^{15}$ is $C_1$–$C_4$-alkyl, $C_1$–$C_4$-haloalkyl, $C_1$–$C_4$-alkoxy, $C_1$–$C_4$-alkoxy-$C_1$–$C_4$-alkyl, $C_1$–$C_4$-alkoxycarbonyl or $C_1$–$C_4$-alkoxycarbonyl-$C_1$–$C_4$-alkyl, or $R^9$ and $R^{10}$ together with the nitrogen atom to which they are attached denote a heterocyclic group having 5 or 6 ring atoms including one or two ring nitrogen atoms, preferably piperazinyl, piperidino, pyrrolidonyl, or one ring nitrogen atom and one ring oxygen atom, preferably morpholino, the heterocyclic group having two ring nitrogen atoms optionally having a $C_1$–$C_4$-alkyl, a hydroxy $C_1$–$C_4$-alkyl, a $C_1$–$C_4$-alkylcarbonyl, a $C_1$–$C_4$-alkoxycarbonyl or $C_1$–$C_4$-alkoxycarbonylalkyl group attached to the nitrogen atom in the —$R^9$—$R^{10}$- radical, and the heterocyclic group having one ring nitrogen atom and one ring oxygen atom optionally having one or two $C_1$–$C_4$-alkyl groups attached to a ring carbon atom, or the third of $R^2$, $R^3$ and $R^4$ is —SO$_2$N($R^{11}$)$R^{12}$ where $R^{11}$ is hydrogen or $C_1$–$C_4$-alkyl and $R^{12}$ is hydrogen, $C_1$–$C_4$-alkyl, hydroxy-$C_1$–$C_4$-alkyl, $C_1$–$C_4$-alkoxy-$C_1$–$C_4$-alkyl or $C_1$–$C_4$-alkoxycarbonyl-$C_1$–$C_4$-alkyl, or $R^{11}$ and $R^{12}$ together with the nitrogen atom to which they are attached denote a heterocyclic group having 6 ring atoms including one or two ring nitrogen atoms, e.g. piperidino or piperazinyl, or one ring nitrogen atom and one ring oxygen atom, e.g. morpholino, the heterocyclic group having two ring nitrogen atoms optionally having a $C_1$–$C_4$-alkyl group attached to the nitrogen atom in the —$R^{11}$—$R^{12}$- radical, or the third of $R^2$, $R^3$ and $R^4$ is $C_1$–$C_4$-alkylene-SO$_2$N($R^{11}$)$R^{12}$ where $R^{11}$ and $R^{12}$ are each independently hydrogen or $C_1$–$C_4$-alkyl, or the third of $R^2$, $R^3$ and $R^4$ is —CON($R^{13}$)$R^{14}$ where $R^{13}$ and $R^{14}$ are each independently hydrogen or $C_1$–$C_4$-alkyl, or (c) the second and third of $R^2$, $R^3$ and $R^4$ are attached to adjacent carbon atoms in the indicated benzene ring and denote, together with said adjacent carbon atoms, a heterocyclic group having 5 to 9 ring atoms, of which one or two are hetero atoms selected from nitrogen, oxygen and sulfur, especially an indazolyl, benzothiazolyl, quinolyl, indolyl, benzofuranonyl or dioxanaphthyl group, and $R^5$ is hydrogen or $C_1$–$C_4$-alkyl.

Other preferred compounds of formula I or III and their salts are those where X is an oxygen atom, $R^1$ is $C_1$–$C_4$-alkyl or $C_3$–$C_{10}$ cycloalkyl, one of $R^2$, $R^3$ and $R^4$ is hydrogen, and either (i) the second of $R^2$, $R^3$ and $R^4$ is hydrogen and the third of $R^2$, $R^3$ and $R^4$ is carboxy, $C_1$–$C_4$-alkoxycarbonyl or —N($R^9$)$R^{10}$ where $R^9$ and $R^{10}$ together with the attached nitrogen atom denote a heterocyclic group having 5 or 6 ring atoms including two ring nitrogen atoms or one ring nitrogen atom and one ring oxygen atom, or (ii) the second and third of $R^2$, $R^3$ and $R^4$ are attached to adjacent carbon atoms on the indicated benzene ring and together with the carbon atoms to which they are attached denote a heterocyclic group having 5 or 6 ring atoms, of which one or two are nitrogen atoms.

Further preferred amongst the compounds of formula I or III and their salts where X is an oxygen atom are those where $R^1$ is $C_1$–$C_4$-alkyl or $C_3$–$C_5$cycloalkyl, one of $R^2$, $R^3$ and $R^4$ is hydrogen and either (a) the second of $R^2$, $R^3$ and $R^4$ is hydrogen and the third of $R^2$, $R^3$ and $R^4$ is carboxy, $C_1$–$C_4$-alkoxycarbonyl or —N($R^9$)$R^{10}$ where $R^9$ and $R^{10}$ together with the attached nitrogen atom denote a heterocyclic group having 6 ring atoms including one ring nitrogen atom and one ring oxygen atom, or (b) the second and third of $R^2$, $R^3$ and $R^4$ are attached to adjacent carbon atoms on the indicated benzene ring and denote, together with said adjacent carbon atoms, a heterocyclic group having 5 ring atoms, of which two are nitrogen atoms.

Another group of preferred compounds of formula I or III and their salts are those where X is a sulfur atom, $R^1$ is $C_1$–$C_4$-alkyl, two of $R^2$, $R^3$ and $R^4$ are hydrogen and the third of $R^2$, $R^3$ and $R^4$ is carboxy, $C_1$–$C_4$-alkoxycarbonyl, or —N($R^9$)$R^{10}$ where $R^9$ is hydrogen or $C_1$–$C_4$-alkyl and $R^{10}$ is —COR$^{15}$ where $R^{15}$ is $C_1$–$C_4$-alkyl, or $R^9$ and $R^{10}$ together with the nitrogen atom to which they are attached denote a heterocyclic group having 5 or 6 ring atoms including one or two ring nitrogen atoms or one ring nitrogen atom and one ring oxygen atom, preferably a heterocyclic group having 6 ring atoms including one ring nitrogen atom and one ring oxygen atom.

The compounds represented by formula I are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid or hydriodic acid, nitric acid, sulfuric acid, phosphoric acid; and organic acids, for example aliphatic monocarboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared from compounds of formula I by known salt-forming procedures.

Compounds of formula I which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of formula I by known salt-forming procedures.

Specific especially preferred compounds of the invention are those described hereinafter in the Examples. Among these, most preferred compounds include those of formula III in which (i) X is NH, $R^1$ is cyclopropyl, $R^2$ and $R^4$ are each hydrogen and $R^3$ is NHCOOC(CH$_3$)$_3$; or (ii) X is NH, $R^1$ is cyclopropyl, $R^2$ and $R^4$ are each hydrogen and $R^3$ is morpholino; or (iii) X is NH, $R^1$ is cyclobutyl, $R^2$ and $R^4$ are each hydrogen and $R^3$ is 4tert-butoxycarbonyl-1-piperazinyl; or (iv) X is NH, $R^1$ is cyclobutyl, $R^2$ and $R^4$ are each hydrogen and $R^3$ is —N(CH$_3$)COCH$_3$; or (v) X is NH, $R^1$ is isopropyl, $R^2$ and $R^4$ are each hydrogen and $R^3$ is —SO$_2$N(CH$_3$)$_2$; or (vi) X is NH, $R^1$ is cyclopropyl, $R^2$ and $R^4$ are each hydrogen and $R^3$ is 4-acetyl-1-piperazinyl; or (vii) X is NH, $R^1$ is tert-butyl, $R^2$ is hydrogen and $R^3$ and $R^4$ together denote —CH$_2$—O—CO—; or (viii) X is O, $R^1$ is cyclobutyl, $R^2$ and $R^4$ are each hydrogen and $R^3$ is —N(CH$_3$)COCH$_3$; or (ix) X is NH, $R^1$ is cyclopropyl, $R^2$ and $R^4$ are each hydrogen and $R^3$ is 4-methyl-1-piperazinyl; or (x) X is NH, $R^1$ is tert-butyl, $R^2$ and $R^4$ are each hydrogen and $R^3$ is —N(CH$_3$)COCH$_3$; or (xi) X is NH, $R^1$ is isopropyl, $R^2$ and $R^4$ are each hydrogen and $R^3$ is —N(CH$_2$CH$_3$)COCH$_3$; or (xii) X is NH, $R^1$ is cyclopropyl, $R^2$ and $R^4$ are each hydrogen and $R^3$ is —N(CH$_3$)COCH$_2$CH$_3$;

the compounds being in free form or in the form of pharmaceutically acceptable salts, particularly hydrochloride or trifluoroacetate salts.

The present invention also provides a process for the preparation of compounds of formula I and their salts which comprises (A) reacting a compound of formula

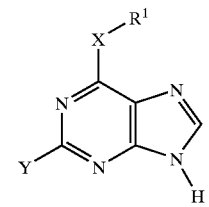

V with a compound of formula

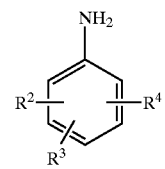

VI where X, $R^1$, $R^2$, $R^3$ and $R^4$ are as hereinbefore defined and Y is a leaving group, preferably halogen such as bromine, iodine or, in particular chlorine, a free functional group in the compounds of formulae V and VI other that those involved in the reaction being protected, if necessary, by a removable protecting group; or (B) for the preparation of a compound of formula I where $R^2$, $R^3$ or $R^4$ is a carboxy or carboxyalkyl group, cleaving a corresponding compound of formula I in which $R^2$, $R^3$ or $R^4$ is an alkoxycarbonyl or alkoxycarbonylalkyl group respectively; or (C) for the preparation of a compound of formula I where $R^2$, $R^3$ or $R^4$ is an alkoxycarbonyl or alkoxycarbonylalkyl group, appropriately esterifying a corresponding compound of formula I in which $R^2$, $R^3$ or $R^4$ is a carboxy or carboxyalkyl group; or (D) for the preparation of a compound of formula I where $R^2$, $R^3$ or $R^4$ is a group of formula —SO$_2$N($R^{11}$)$R^{12}$ as hereinbefore defined, appropriately aminating a corresponding compound of formula

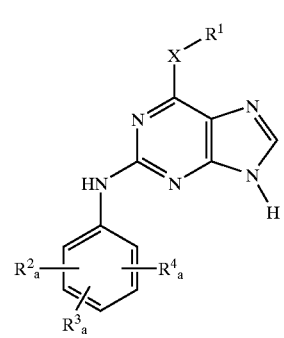

VII where $R^1$ is as hereinbefore defined and $R^2_a$, $R^3_a$ and $R^4_a$ are respectively the same as $R^2$, $R^3$ and $R^4$ as hereinbefore defined, with the exception that at least one of them is a group of formula —SO$_2$—Hal, where Hal is halogen, preferably chlorine or bromine; or (E) for the preparation of a compound of formula I where R$^2$, R$^3$ or R$^4$ is a group of formula —CON(R$^{13}$)R$^{14}$ as hereinbefore defined, appropriately aminating a corresponding compound of formula I where R$^2$, R$^3$ or R$^4$ is a carboxy group;

and optionally converting a resultant compound of formula I in protected form into a corresponding compound in unprotected form;

and recovering the resultant compound of formula I in free or salt form.

Protecting groups, their introduction and their removal are described, for example, in "Protective Groups in Organic Synthesis", T. W. Greene et al., John Wiley & Sons Inc, Second Edition, 1991.

Process variant (A) can be carried out using conventional procedures. It is conveniently, carried out in an inert organic solvent, preferably a polar solvent such as dioxan or N-methylpyrrolidone. The reaction temperature is conveniently from 50 to 250° C., preferably from 100 to 150° C. The reaction may be catalysed by a strong acid, a tertiary base or, preferably, metal ions such as Ag, Cu, Li, Ni, Zn, La, Yb or Sn. The reaction is conveniently carried out using 1 to 5 equivalents, for example 1 to 3 equivalents, of the compound of formula VI, per equivalent of the compound of formula V.

Compounds of formulae V and VI are known or may be prepared by methods analogous to those used for preparation of the known compounds. Thus compounds of formula V may be prepared, for example, as described in WO97/16452 or as described hereinafter in the Examples.

Process variant (B) may be carried out by conventional methods for ester cleavage, for example using conventional acid- or base-catalysed hydrolysis, or analogously as described hereinafter in the Examples.

Process variant (C) may be effected using conventional esterification procedures or analogously as described hereinafter in the Examples.

Process variant (D) may be effected by conventional procedures, for example by reaction of the halosulfonyl compound of formula VII with a compound of formula HN(R$^{11}$)R$^{12}$ where R$^{11}$ and R$^{12}$ are as hereinbefore defined under known conditions or analogously as described hereinafter in the Examples. Compounds of formula VII are known or may be prepared by methods analogous to those used for the preparation of known compounds, for example by reacting a corresponding compound, which is unsubstituted in the position on the benzene ring where the halosulfonyl group is to be introduced, with a halosulfonating agent such as chlorosulfonic acid, e.g. as described hereinafter in the Examples.

Process variant (E) may be effected by conventional methods, for example by conversion of the corresponding carboxy compound into an acid halide and reacting the acid halide with a compound of formula HN(R$^{13}$)R$^{14}$ where R$^{13}$ and R$^{14}$ are as hereinbefore defined under known conditions or analogously as described hereinafter in the Examples.

Compounds of formula I in free form may be converted into salt form, and vice versa, in a conventional manner. The compounds in free or salt form can be obtained in the form of hydrates or solvates containing a solvent used for crystallization.

Compounds of formula I can be recovered from the reaction mixture and purified in a conventional manner.

Isomer mixtures can be separated into individual isomers, e.g. enantiomers, in a conventional manner, e.g. by fractional crystallization.

Compounds of formula I in free or salt form are useful as pharmaceuticals. Accordingly the invention also provides a compound of formula I in free or pharmaceutically acceptable salt form for use as a pharmaceutical. The compounds of formula I in free or pharmaceutically acceptable salt form, hereinafter referred to alternatively as "agents of the invention", inhibit the activity of the tyrosine protein kinase syk, which is an activator of pro-inflammatory cells driving an allergic response. This inhibitory property of the agents of the invention can be demonstrated in the following assay:

In this assay the effect of an agent of the invention on the phosphorylation of a peptide by syk kinase is determined. The phosphate is transferred from the terminal phosphate of adenosine triphosphate (ATP) to the biotin-modified peptide biotin-EDPDYEWPSA (available from Genosys) which is a known specific substrate for syk. When $^{33}$P-phosphorylated peptide binds to streptavidin-polyvinyltoluene (PVT) Scintillation Proximity Assay (SPA) beads (available from Amersham), the emitted β-particles excite the fluorophore in the beads and produce light. Free $^{33}$P-ATP in solution does not excite the fluorophore because the beads are separated from solution by flotation and so it is not in dose proximity to the beads. The scintillation count is therefore a measure of the extent to which the test compound inhibits phosphorylation by syk kinase.

To the wells of an Optiplate (Canberra Packard) are added (i) the compound under test in DMSO/distilled water (10 µl), (ii) 20 µl of a composition formed by mixing 1 mM biotin-EDPDYEWPSA (5.5 µl), 300 µM ATP (18.3 µl), and $^{33}$P-ATP in sufficient amount to add 0.1 µCi $^{33}$P-ATP per well (1.1 µl on the day of production) and making up the volume to 2.2 ml with a buffer (Buffer A) prepared by dissolving tris-base (0.36 g) in distilled water (80 ml), adjusting the pH to 7.5 with 1M hydrochloric acid, adding 1M aqueous MgCl$_2$ (1.5 ml), 50 mM aqueous sodium orthovanadate (30 µl) and 1M aqueous dithiothrietol (150 µl), and making the volume up to 120 ml with distilled water, (iii) 0.5% w/v syk kinase in Buffer A (20 µl). The plate is incubated at room temperature for 30 minutes with shaking, the reaction is then terminated by addition to all wells of 150 µl of a mixture prepared by reconstituting 500 mg Streptavidin-PVT SPA beads in 373 ml of Tris-buffered saline containing 673.6 g cesium chloride, 20 ml 0.5M EDTA and 27.5 mg ATP (disodium salt) per litre. The plate is again incubated at room temperature for 30 minutes with shaking, then sealed using Top Seal-S (Canberra Packard) according to the manufacturer's instructions and left to stand at room temperature for 1 hour. The resulting scintillations are counted using a Packard TopCount, each well being counted for 1 minute.

The procedure is repeated for different concentrations of test compound selected to cover the range of 0% to 100% inhibition and the concentration at which 50% inhibition of syk kinase phosphorylation occurs (IC$_{50}$) for each compound is determined from concentration-inhibition curves in a conventional manner.

The compounds of the Examples hereinbelow have IC$_{50}$ values of the order of 1 µM or less in the above assay. For instance, the compounds of Examples 1 to 7 hereinbelow have IC$_{50}$ values of 3 nM, 4 nM, 5 nM, 5 nM, 9 nM, 10 nM and 10 nM respectively, the compounds of Examples 102 to 104 have IC$_{50}$ values of 5 nM, 2 nM and 3.6 nM respectively and the compunds of Examples 138, 141, 170, 172, 188 and 201 have IC$_{50}$ values of 14 nM, 4.5 nM, 10 nM, 6 nM, 5 nM and 5 nM respectively.

Having regard to their inhibition of syk kinase, and their suppression of IgE-mediated degranulation of mast cells, the agents of the invention are useful in the treatment of conditions which are mediated by syk kinase, particularly inflammatory or allergic conditions. Treatment in accordance with the invention may be symptomatic or prophylactic.

Accordingly, the agents of the invention are useful in the treatment of inflammatory or obstructive airways diseases. Inflammatory or obstructive airways diseases to which the present invention is applicable include asthma of whatever type or genesis including both intrinsic (non-allergic) asthma and extrinsic (allergic) asthma. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include adult respiratory distress syndrome (ARDS), chronic obstructive pulmonary or airways disease (COPD or COAD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their anti-inflammatory activity, in particular in relation to inhibition of cosinophil activation, agents of the invention are also useful in the treatment of eosinophil related disorders, e.g. cosinophilia, in particular eosinophil related disorders of the airways (e.g. involving morbid eosinophilic infiltration of pulmonary tissues) including hypereosinophilia as it effects the airways and/or lungs as well as, for example, cosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Agents of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin.

Agents of the invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, and inflammatory bowel disease such as ulcerative colitis and Crohn's disease.

The effectiveness of an agent of the invention in inhibiting inflammatory conditions, for example in inflammatory airways diseases, may be demonstrated in an animal model, e.g. a mouse or rat model, of airways inflammation or other inflammatory conditions, for example as described by Szarka et al, J. Immunol. Methods (1997) 202:49–57; Renzi et al, Am. Rev. Respir. Dis. (1993) 148:932–939; Tsuyuki et al., J. Clin. Invest. (1995) 96:2924–2931; and Cemadas et al (1999) Am. J. Respir. Cell Mol. Biol. 20:1–8.

The agents of the invention are also useful as co-therapeutic agents for use in conjunction with anti-inflammatory or bronchodilatory drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with the anti-inflammatory or bronchodilatory drug in a fixed pharmaceutical composition or it may be administered separately, before, simultaneously with or after the anti-inflammatory or bronchodilatory drug. Such anti-inflammatory drugs include steroids, in particular glucocorticosteroids such as budesonide, beclamethasone, fluticasone or mometasone, and dopamine receptor agonists such as cabergoline, bromocriptine or ropinirole. Such bronchodilatory drugs include anticholinergic or antimuscarinic agents, in particular ipratropium bromide, oxitropium bromide and tiotropium bromide. Combinations of agents of the invention and steroids may be used, for example, in the treatment of COPD or, particularly, asthma. Combinations of agents of the invention and anticholinergic or antimuscarinic agents or dopamine receptor agonists may be used, for example, in the treatment of asthma or, particularly, COPD.

In accordance with the foregoing, the invention also provides a method for the treatment of a condition mediated by syk kinase, for example an inflammatory or allergic condition, particularly an inflammatory or obstructive airways disease, which comprises administering to a subject, particularly a human subject, in need thereof an effective amount of a compound of formula I in a free or pharmaceutically acceptable salt form as hereinbefore described. In another aspect the invention provides a compound of formula I, in free or pharmaceutically acceptable salt form, as hereinbefore described for use in the manufacture of a medicament for the treatment of a condition mediated by syk kinase.

The agents of the invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

In a further aspect, the invention also provides a pharmaceutical composition comprising a compound of formula I in free or pharmaceutically acceptable salt form together with a pharmaceutically acceptable diluent or carrier therefor. The composition may contain a co-therapeutic agent such as an anti-inflammatory or bronchodilatory drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

The invention includes (A) an agent of the invention in inhalable form, e.g. in an aerosol or other atomisable composition or in inhalable particulate, e.g. micronised form, (B) an inhalable medicament comprising an agent of the invention in inhalable form; (C) a pharmaceutical product comprising such an agent of the invention in inhalable form in association with an inhalation device; and (D) an inhalation device containing an agent of the invention in inhalable form.

Dosages of agents of the invention employed in practising the present invention will of course vary depending, for example, on the particular condition to be treated, the effect desired and the mode of administration. In general, suitable daily dosages for administration by inhalation are of the order of 0.1 to 100 mg/kg while for oral administration suitable daily doses are of the order of 1 to 1000 mg/kg.

The invention is illustrated by the following Examples.

EXAMPLES

Intermediates used in the Examples are prepared as follows:

1. Meta-(3,5-dimethylmorpholino) aniline a. Meta-(3,5-dimethylmorpholino) nitrobenzene 1-Fluoro-3-nitrobenzene (2.8 g, 0.02M) and 2,6-dimethylmorpholine (12.5 g, 0.12M) are heated in DMSO (33 ml) at 100° C. for 66 hours. The cooled mixture is poured into water (300 ml). The precipitate is collected by filtration, washed with water and dried under vacuum; ES+ (M+Na) 258.96; mp 126.6–127.8° C.

b. Meta-(3,5-dimethylmorpholino) aniline

Meta-(3,5dimethylmorphohno) nitrobenzene (1a) (2 g, 8.5 mmol) is hydrogenated in ethanol (50 ml), over 10%Pd on carbon (200 mg) for 1.5 hours. The catalyst is removed by filtration and the solvent removed evaporation to yield an oil. The enantiomers can be separated by silica column chromatography. ES+ (M+1) 207.36.

2. Meta-morpholino aniline a. Meta-morpholino nitrobenzene

Using 1-fluoro-3-nitrobenzene (10 g, 0.07M) and morpholine (33.5 g, 0.38M) in DMSO (116 ml) is prepared using the method described by Brown G. R. et al., Tet. Lett. 40 (1999) 1219–1222. Filtration of the precipitated product yields the product; mp 113.8–115.5° C.

b. Meta-morpholino aniline

Meta-morpholino nitrobenzene (2a) (2 g, 9.6 mmol) is hydrogenated in a mixture of ethanol and ethyl acetate (50 ml/10 ml), over 10% Pd on carbon (200 mg) for 1 hour. The catalyst is removed by filtration and the solvent removed by evaporation to yield a solid, which is dried under vacuum; ES+ (M+1) 179.35; mp 125.4–127.6° C.

3. Meta-(1-methylpiperazine) aniline a. Meta-(1-methylpiperazine) nitrobenzene

1-Fluoro-3-nitrobenzene (8.5 ml, 0.08M) and 1-methyl piperazine (22.5 ml, 0.247M) are heated in DMSO(100 ml) at 100° C. for 48 hours. The cooled mixture is poured into water (500 ml). The aqueous mixture is cooled at 0° C. and after 48 hours the precipitate is collected by filtration, washed with cold water and dried under vacuum; ES+ (M+1) 222, mp 107.5–108.2° C.

b. Meta-(1-methylpiperazine) aniline

Meta-(1-methylpiperazine) nitrobenzene (3a) (2 g, 0.009M) is hydrogenated in ethanol (50 ml), over 10%Pd on carbon (100 mg) for 0.5 hours. The catalyst is removed by filtration and the solvent removed by evaporation to yield an oil; ES+ (M+1) 191.5; mp.87.6–89.0° C.

4. Para-(1-methylpiperazine) aniline a. Para-(1-methylpiperazine) nitrobenzene

1-Fluoro-4-nitrobenzene (8.5 ml, 0.08M) and 1-methyl piperazine (22.5 ml, 0.247M) are heated in DMSO(100 ml) at 100° C. for 60 hours. The cooled mixture is poured into water (500 ml) and the precipitate collected by filtration, washed with water and dried under vacuum; ES+ (M+1) 222; mp 57.4–58.9° C.

b. Para-(1-methylpiperazine) aniline

Para-(1-methylpiperazine) nitrobenzene (4a) (2 g, 0.009M) is hydrogenated in ethanol (50 ml), over 10%Pd on carbon (250 mg) for 5 hours. The catalyst is removed by filtration and the solvent removed by evaporation to yield a solid. ES+ (M+1) 191.8; mp 101.5–103.4° C.

Intermediates 5a to 8b of formula

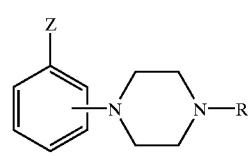

VIII where Z is $NO_2$ or $NH_2$ and the substituted piperazinyl group is meta or para to Z are prepared analogously to those above. These are shown in the following table, together with the analogous method of preparation:

| No. | Z | meta/para | R | Method | ES+ (M+1) | mp (° C.) |
|---|---|---|---|---|---|---|
| 5a | $NO_2$ | m- | $COCH_3$ | 3(a) |  | 151.3–153.6 |
| 5b | $NH_2$ | m- | $COCH_3$ | 3(b) | 220 | 127.8–129.4 |
| 6a | $NO_2$ | p- | $COCH_3$ | 4(a) | 250 | 98.2–101.3 |
| 6b | $NH_2$ | p- | $COCH_3$ | 4(b) | 220 | 138.8–140.7 |
| 7a | $NO_2$ | m- | $COC(CH_3)_3$ | 3(a) |  | 146.1–147.0 |
| 7b | $NH_2$ | m- | $COC(CH_3)_3$ | 3(b) |  |  |
| 8a | $NO_2$ | p- | $COC(CH_3)_3$ | 4(a) |  | 88.4–90.1 |
| 8b | $NH_2$ | p- | $COC(CH_3)_3$ | 4(b) | 278 |  |

9. N-acetyl-N-ethyl 4-aminoaniline a. N-acetyl-N-ethyl-4nitroaniline

To a suspension of N-ethyl 4-nitroaniline (1.5 g, 9.026 mmol) in benzene (15 ml), is added acetylchloride (10 ml) and the mixture refluxed for 40 minutes. The solvent is removed by evaporation. The residue is dissolved in ethyl acetate prior to washing with 2N sodium bicarbonate and water, drying ($MgSO_4$) and evaporation. The product is dried under vacuum; ES+ (M+1) 208.57.

b. N-acetyl-N-ethyl-4-aminoaniline

N-acetyl-N-ethyl-4-nitroaniline (9a) (1.8 g, 8.64 mmol) is hydrogenated in THF (30 ml), over 10%Pd on carbon (100 mg) for 1.5 hours. The catalyst is removed by filtration and the solvent removed evaporation. The product crystalises on standing in hexane, and following filtration, is dried under vacuum; ES+ (M+1) 178.88.

10. N-propionyl-N-methyl-4-aminoaniline a. N-propionyl-N-methyl-4-nitroaniline

The reaction is carried out using an analogous method to (9a), using N-methyl-4 nitroanilinc (5 g, 32.86 mmol) in benzene (30 ml), treated with propionyl chloride (15 ml). ES+ (M+1) 208.88.

b. N-propionyl-N-methyl-4-aminoaniline

The reaction is carried out using an analogous method to (9b), using N-propionyl-N-methyl-4-nitroaniline (10a)(6.8 g, 32.86 mmol), 10%Pd on carbon (447 mg) in THF (75 ml). The hydrogenation yields an oil. ES+ (M+1) 178.87.

11. 4-(Ethyloxalylamido) aniline a. 4-(Ethyloxalylamido)-1-tert-butyl carboxylate aniline

To a solution of N-tert-butyl carboxylate-1,4-phenylenediamine (1 g, 4.8 mmol) and triethylamine (1.34 ml) in dichloromethane (15 ml), is added ethyl oxalyl chloride (0.655 g, 4.8 mmol) at 10° C. The mixture is stirred at ambient temperature for 10 minutes. The mixture is partitioned between dichloromethane and water. The organic layer is separated and washed with water, dried ($MgSO_4$) and evaporated. The residue is suspended in diethyl ether and hexane. Following filtration and washing with further diethyl ether/hexane, the product is dried under vacuum.

b. 4-(Ethyloxalylamido) aniline

To a solution of 4-(ethyloxalylamido)-1-tert-butyl carboxylate aniline (11a)(1.3 g, 4.2 mmol) in dichloromethane (25 ml) at 10° C., is added trifluoroacetic acid (5 ml) and stirred for 48 hours at 5° C. The mixture is basified with the addition of conc. ammonium hydroxide and diluted with ethyl acetate (200 ml). This is washed with water/ice and with brine, dried ($MgSO_4$) and evaporated prior to purification by silica column chromatography. The product is obtained as orange crystals; mp 110–113° C.

12. 4(Methyl malonylamido) aniline a. 4-(Methyl malonylamido)-1-tert-butyl carboxylate aniline

To a solution of N-tert-butyl carboxylate-1, 4phenylenediamine (1 g, 4.8 mmol) and triethylamine (2 ml) in dichloromethane (15 ml), is added methyl malonyl chloride (1 ml, 9.6 mmol) at 10° C. The mixture is stirred at ambient temperature for 1 hour and then at 40° C. for 30 minutes. The suspension is partitioned between dichloromethane and water. The organic layer is separated and washed with water, dried ($MgSO_4$) and evaporated. The product is purified by silica column chromatography.

b. 4(Methyl malonylamido) aniline

To a solution of 4-(methyl malonylamido)-1-tert-butyl carboxylate aniline (12a)(1.3 g, 4.2 mmol) in dichloromethane (25 ml) at 10° C., is added trifluoroacetic acid (5 ml) and stirred for 48 hours at 5° C. The biphasic mixture is stirred at 0° C. and basified with the addition of conc. ammonium hydroxide and diluted with ethyl acetate (200 ml). This is washed with waterlice and with brine, dried ($MgSO_4$) and evaporated prior to purification by silica column chromatography. The product is obtained as yellow crystals; mp 103–105° C.

13. 4-Butylamido aniline a. 4-(Butylamido)-1-tert-butyl carboxylate aniline

To a solution of N-tert-butyl carboxylate-1,4-phenylenediamine (0.6 g, 2.88 mmol) and triethylamine (0.803 ml) in dichloromethane (10 ml), is added butyryl chloride (0.299 ml, 2.88 mmol) at 10° C. The mixture is stirred at ambient temperature for 1 hour. The suspension is partitioned between dichloromethane and water. The organic layer is separated and washed with water, dried ($MgSO_4$) and evaporated to yield a crystalline product; ES+ (M+Na) 301.23.

b. 4-(Butylamido) aniline

To a solution of 4-(butylamido)-1-tert-butyl carboxylate aniline (13a)(0.77 g, 2.77 mmol) in dichloromethane (75 ml) at 10° C., is added trifluoroacetic acid (2 ml) and stirred for 18 hours at ambient temperature. The biphasic mixture is stirred at 0° C. and basified with the addition of conc. ammonium hydroxide. This is washed with water, dried ($MgSO_4$) and evaporated prior to purification by silica column chromatography. The product is obtained in crystalline form.

14. N-Methyl cyclopropylamine a. N-Carbobenzyloxy cyclopropylamine

The synthesis of N-carbobenzyloxy cyclopropylamine is carried out according to the method outlined in J. Heterocycl. Chem (1983), 1035, using carbobenzyloxychloride (56.3 g, 0.33M), cyclopropylamine (19.6 g, 0.344M), sodium carbonate (36.1 g, 0.34M) in toluene (400 ml) and water (400 ml). The product is obtained as colourless crystals; ES+ (M+1) 192.6.

b. N-Methyl-N-carbobenzyloxy cyclopropylamine

The synthesis of N-carbobenzyloxy cyclopropylamine is carried out according to the method outlined in J. Heterocycl. Chem (1983), 1035, using N-carbobenzyloxy cyclopropylamine (14a)(10.5 g, 0.055M) in DMF (80 ml), sodium hydride(1.4 g) and methyl iodide (4 ml). The product is purified by vacuum distillation. Bp 86–92° C., 0.02 Torr.

c. N-Methyl cyclopropylamine

The sythesis of N-methyl cyclopropylamine is carried out according to the method outlined in J. Heterocycl. Chem (1983), 1035, using N-methyl-N-carbobenzyloxy cyclopropylamine(14b)(11.45 g, 0.055M), concentrated hydrochloric acid(4.32 ml), 10%Pd on carbon (700 mg) in ethanol(135 ml). The product is obtained and used as an ethereal solution.

15. Para-(1-ethylpiperazine) aniline a. Para-(1-ethylpiperazine) nitrobenzene

1-Fluoro-4nitrobenzene (0.54 ml, 0.005M), 1-ethyl piperazine (1.9 ml, 0.015M) and potassium carbonate (0.69 g, 0.005M) are heated in acetonitrile (7 ml) at 85° C. under $N_2$ for 24 hours. The cooled mixture is partitioned between dichloromethane and water. The organic layer is separated and the aqueous extracted twice with dichloromethane. The combined organics are washed twice with brine, dried ($MgSO_4$), filtered and evaporated to yield a solid, which can be purified further by column chromatography if required. ES+(M+1) 236; mp. 79–81° C.

b. Para-(1-ethylpiperazine) aniline

Para-(1-ethylpiperazine) nitrobenzene (0.5 g, 0.002M) is hydrogenated in ethanol/ethyl acetate mixture (12.5 ml/2.5 ml), over 10% Pd on carbon (50 mg) for 24 hours. The catalyst is removed by filtration and the solvent removed by evaporation to yield a solid which is dried under vaccum. ES+(M+1) 206; mp. 77–78° C.

Intermediates 16a to 18b of formula VIII are prepared analogously to 15a and 15b. These are shown in the following table.

| No. | Z | meta/para | R | Method | ES+ (M+1) | mp (° C.) |
|---|---|---|---|---|---|---|
| 16a | $NO_2$ | p- | $CH_2CH_2OH$ | 15(a) | 252 | 98–100.5 |
| 16b | $NH_2$ | p- | $CH_2CH_2OH$ | 15(b) | 222 | — |
| 17a | $NO_2$ | p- | $CH_2COOCH_2CH_3$ | 15(a) | — | — |
| 17b | $NH_2$ | p- | $CH_2COOCH_2CH_3$ | 15(b) | 264 | — |
| 18a | $NO_2$ | p- | $COOCH_2CH_3$ | 15(a) | — | 114–117 |
| 18b | $NH_2$ | p- | $COOCH_2CH_3$ | 15(b) | — | — |

Para-(1-hydroxypiperidine) nitrobenzene (19(a)) is prepared from 1-fluoro-4-nitrobenzene and 4-hydroxypiperidine analogously to 15(a); ES+(M+1) 223.

Para-(1-hydroxypiperidine) aniline (19(b)) is prepared analogously to 15(b) from 19(a); TOF ES+(M+1)193.

20. 1-(4Anilino)-2-pyrrolidione 1-(4-nitrophenyl)-2-pyrrolidione (1 g, 0.004M) is hydrogenated in ethyl acetate (75 ml), over 5% Pd on carbon (160 mg) for 18 hours. The catalyst is removed by filtration and the solvent removed by evaporation to yield a solid. ES+(M+1) 177; mp.129–130° C.

21. 3,3-Dimethyl-1-(4-anilino)-2-azetidinone 3,3-Dimethyl-1-(4nitrophenyl)-2-azetidinone (985 mg, 0.004M) is hydrogenated in ethyl acetate (100 ml), over 5% Pd on carbon (150 mg) for 1 hour. The catalyst is removed by filtration and the solvent removed by evaporation to yield a solid. ES+(M+1)191; mp.113–114° C.

Compounds of formula III are prepared by one of the following general methods:

Method A: The corresponding 2-chloro-6-substituted purine of formula V is heated with 1.5 to 3 equivalents of the appropriate aniline of formula VI at temperatures between 90 and 190° C. for times between 3 and 78 hours. The required product is isolated by (i) precipitation from the reaction mixture, washing with methanol, ethanol, water or dioxan and optionally isolation of a hydrochloride salt by treatment with HCl in dioxan or (ii) concentration from methanol or ethanol or (iii) concentration followed by flash silica chromatopgraphy or direct purification by preparative HPLC.

Method B: As Method A, except that the purine of formula V is heated with 1.5 equivalents of the aniline of formula VI and 1.5 equivalents of diisopropylethylamine at 130° C. for 16–96 hours and the product is isolated by partitioning between ethyl acetate and water, followed by extraction with ethyl acetate, concentration and purification by flash silica chromatography.

Method C: As Method A, except that the reaction mixture is partitioned between ethyl acetate and water, basified with 1N NaOH or saturated aqueous $NaHCO_3$, extracted with ethyl acetate, concentrated and purified by flash silica chromatography.

Method D: The corresponding ester in ethanol, THF/aqueous methanol or THF/water is treated with 2.5 to 13 equivalents of 1N NaOH or LiOH at room temperature. The mixture is neutralised with 1N hydrochloric acid and solvent removed. The product is isolated by dissolution in ethanol, filtration and evaporation of the filtrate.

Method E: As method A, with the addition of concentrated hydrochloric acid or trifluoroacetic acid to the heated reaction mixture.

Method F: As Method A, followed by treatment of the product with chlorosulfonic acid. 400 µL of a solution of the resulting sulfonyl chloride is added to a 1M solution of the appropriate amine of formula $HN(R^{11})R^{12}$ and, after 2 hours, the solvent is removed and the product purified by preparative HPLC.

Method G: As Method A, with the addition of silver triflate (1 equivalent) to the heated reaction mixture.

Method H: The corresponding carboxylic acid is stirred in DMF, with 1 equivalent of the appropriate amine of formula $HN(R^{13})R^{14}$ dissolved in THF, and equivalent amounts of N-dimethylaminopyridine and benzotriazol-1-yl-oxy-tris-pyrrolidino-phosphonium hexafluorophosphate at 20° C. for 16 hours. The product is isolated by precipitation from the reaction mixture on treatment with 1N hydrochloric acid, followed by purification by flash silica chromatography.

Method I: The corresponding carboxylic acid is reacted with excess thionyl chloride to give the corresponding acid chloride, which is treated with the appropriate amine of formula $HN(R^{13})R^{14}$, or appropriate alcohol, in benzene. The product is isolated by evaporation, and purified by preparative HPLC.

Method J: The corresponding 2-chloro-6-substituted purine of formula V and the appropriate aniline of formula VI (2.2 equivalents) are microwaved at 140° C., 50% power, for 10 minutes, followed by trituration with methanol. The product is isolated by filtration.

The prepared compounds of formula III, designated Examples 1 to 221, are shown in the table below, together with the general method used. In the table, CyPr denotes cyclopropyl, CyBu denotes cyclobutyl, CyPe denotes cyclopentyl and BnPp denotes N-benzylpiperidyl.

| Ex. | X | $R^1$ | $R^2$ | $R^3$ | $R^4$ | Method |
|---|---|---|---|---|---|---|
| 1 | NH | CyPr |  | —CH=N—NH— | H | A |
| 2 | NH | CyPr | H | —CH=N—NH— |  | A |
| 3 | NH | CyPr | H | NHCOOC(CH$_3$)$_3$ | H | C |
| 4 | NH | CH$_3$CH$_2$— | H | —CH=N—NH— |  | A |
| 5 | NH | CyPr | H | 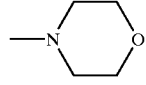 | H | B |
| 6 | NH | CyBu | H | —N(CH$_3$)COCH$_3$ | H | A |
| 7 | NH | CyBu |  | —NH—N=CH— | H | A |
| 8 | NH | CyPrCH$_2$— | H | —CH=N—NH— |  | A |
| 9 | NH | CyPr | H | —CONHCH(CH$_3$)$_2$ | H | C |
| 10 | NH | CH$_3$CH$_2$— | H | —N(CH$_3$)COCH$_3$ | H | A |
| 11 | NH | CyPr | H | 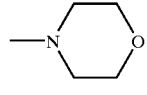 | H | B |
| 12 | NH | CyBu | H | —NH—N=CH— |  | A |
| 13 | NH | CyPr | H | —N(CH$_3$)COCH$_3$ | H | A |
| 14 | O | CyBu |  | —CH=N—NH— | H | A |
| 15 | NH | (CH$_3$)$_3$C— |  | —CH=N—NH— | H | E |
| 16 | NH | CyPrCH$_2$— |  | —NH—N=CH— | H | E |
| 17 | NH | CyPrCH$_2$— | H | —N(CH$_3$)COCH$_3$ | H | A |
| 18 | O | CyBu |  | —NH—N=CH— | H | E |
| 19 | NH | CyPr | H | —COOCH$_3$ | H | C |
| 20 | NH | CyBu | H | —CONHCH(CH$_3$)$_2$ | H | C |
| 21 | NH | CyBu | H | —CH=N—N(CH$_3$)— |  | A |
| 22 | NH | CyPr | H | —CH=N—N(CH$_3$)— |  | A |
| 23 | NH | CyBu | H | —NHCOCH$_2$COOCH$_3$ | H | A |
| 24 | NH | —CH$_2$—CH=CH$_2$ |  | —CH=N—NH— | H | E |
| 25 | N(CH$_3$) | CyPr |  | —NH—N=CH— | H | E |
| 26 | NH | CyBu | H | —COOCH$_3$ | H | C |
| 27 | NH | CyPr | H | H | H | A |
| 28 | NH | (CH$_3$)$_2$CH— | H | —N(CH$_3$)COCH$_3$ | H | A |
| 29 | NH | CyPr | H | —CH$_2$COOCH$_2$CH$_3$ | H | C |
| 30 | NH | CyPr | H | —CH$_2$COOCH$_2$CH$_3$ | H | C |
| 31 | NH | CH$_2$CH$_2$OH | H | —N(CH$_3$)COCH$_3$ | H | A |
| 32 | NH | CH$_2$CH$_2$OH | H | 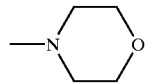 | H | A |
| 33 | NH | CyBu | H | —NHCOCH$_3$ | H | A |
| 34 | N(CH$_3$) | CyPr |  | —CH=N—NH— | H | E |
| 35 | N(CH$_3$) | CyPr | H | —N(CH$_3$)COCH$_3$ | H | A |
| 36 | NH | CyPe | H | —N(CH$_3$)COCH$_3$ | H | A |
| 37 | NH | CyBu | H | 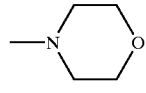 | H | C |
| 38 | NH | CyBu | H | —NH$_2$ | H | C |
| 39 | NH | BnPp | —OCH$_3$ | H | —OCH$_3$ | E |
| 40 | N(CH$_3$) | CH$_3$ | H | —N(CH$_3$)COCH$_3$ | H | A |
| 41 | NH | CyPr | H | H | —OCH$_3$ | A |
| 42 | NH | CyBu | H | —NHCH$_3$ | H | A |
| 43 | NH | CyBu | H | —NHCO(CH$_2$)$_2$CH$_3$ | H | A |
| 44 | NH | CyPr | —OCH$_3$ | H | —OCH$_3$ | A |
| 45 | NH | CyPr | H | H | —SO$_2$NH$_2$ | A |
| 46 | NH | CyBu | H | —NHCOOC(CH$_3$)$_3$ | H | C |

-continued

| Ex. | X | R¹ | R² | R³ | R⁴ | Method |
|---|---|---|---|---|---|---|
| 47 | N(CH₃) | CH₃ | H | (N-morpholinyl) | H | A |
| 48 | NH | CyPr | H | —CH₂COOH | H | D |
| 49 | NH | CyBu | H | —CH₂COOCH₂CH₃ | H | C |
| 50 | NH | CyPr | H | H | (N-piperidinyl)-(CH₂)₂OH | B |
| 51 | NH | CyBu | H | H | —OCH₃ | E |
| 52 | NH | CyPr | H | H | —COOCH₂CH₃ | C |
| 53 | NH | (CH₃)₂CH— | H | H | —OCH₃ | E |
| 54 | NH | CyPr | —OCH₃ | —OCH₃ | —OCH₃ | A |
| 55 | NH | CyPe | H | H | —OCH₃ | A |
| 56 | NH | CyBu | H | H | —COOCH₂CH₃ | C |
| 57 | NH | CyPe | H | H | —OCH₃ | A |
| 58 | NH | CyBu | H | —CH₂COOH | H | D |
| 59 | NH | CyBu | H | H | (N-piperidinyl)-(CH₂)₂OH | B |
| 60 | NH | BnPp | H | —N(CH₃)COCH₃ | H | E |
| 61 | NH | CyBu | H | H | —COOH | D |
| 62 | NH | BnPp | H | H | H | A |
| 63 | NH | 6-(1H-indazolyl) | —OCH₃ | H | —OCH₃ | A |
| 64 | NH | 2-tetrahydronaphthyl | H | CH₂SO₂NHCH₃ | H | A |
| 65 | NH | CyPr | H | —NH₂ | H | D |
| 66 | NH | 1-hydroxy-1-carbonyl-cyclopropyl | H | —N(CH₃)COCH₃ | H | D |
| 67 | NH | CH₃ | H | —N(CH₃)COCH₃ | H | A |
| 68 | NH | 1-(COOCH₂CH₃)-cyclopropyl | H | —N(CH₃)COCH₃ | H | A |
| 69 | NH | 1-(COOCH₂CH₃)-cyclopropyl | —NH—N=CH— | | H | A |
| 70 | NH | —CH₂CH₃ | H | (N-morpholinyl) | H | A |
| 71 | NH | CH₃ | H | (N-morpholinyl) | H | A |
| 72 | NH | CyBu | H | —NHCOCOCH₂CH₃ | H | A |
| 73 | NH | —CH₂CH₃ | H | —COOCH₃ | H | A |
| 74 | NH | CyBu | H | —SO₂NH₂ | H | F |

-continued

| Ex. | X | R¹ | R² | R³ | R⁴ | Method |
|---|---|---|---|---|---|---|
| 75 | NH | CyBu | H | —SO₂NHCH₃ | H | F |
| 76 | NH | CyBu | H | —SO₂N(CH₃)₂ | H | F |
| 77 | NH | CyBu | H | —SO₂N(morpholino) | H | F |
| 78 | NH | CyBu | H | —SO₂NHCH₂CH₂OCH₃ | H | F |
| 79 | NH | —CH₂CH₃ | H | —COOH | H | D |
| 80 | NH | —CH₂CH₃ | H | —CONHCH₂CH₃ | H | H |
| 81 | NH | CyPr | H | —CONHCH₃ | H | C |
| 82 | NH | CyPr | H | H | —CONHCH₃ | C |
| 83 | NH | CyBu | H | H | —CONHCH₃ | C |
| 84 | NH | —(CH₂)₂CH₃ | H | —N(CH₃)COCH₃ | H | A |
| 85 | NH | —(CH₂)₂CH₃ | H | —N(morpholino) | H | A |
| 86 | NH | —(CH₂)₃CH₃ | H | —N(CH₃)COCH₃ | H | A |
| 87 | NH | —(CH₂)₃CH₃ | H | —N(morpholino) | H | A |
| 88 | NH | CyPr | H | —NHCOCF₃ | H | B |
| 89 | NH | —CH₂CH₃ | H | —CON(CH₃)₂ | H | I |
| 90 | NH | CyBu | H | —N(CH₂CH₃)COCH₃ | H | A |
| 91 | NH | CyPr | H | —N(piperazino-COOC(CH₃)₃) | H | C |
| 92 | NH | CyPr | H | —COOH | H | D |
| 93 | NH | CyBu | H | —COOH | H | D |
| 94 | NH | —CH₂CH₃ | H | —COOCH(CH₃)₂ | H | I |
| 95 | NH | CyBu | H | —N(CH₃)COCH₂CH₃ | H | A |
| 96 | O | CyBu | H | —N(CH₃)COCH₃ | H | G |
| 97 | O | CyBu | H | —COOCH₃ | H | G |
| 98 | O | CyBu | H | —N(morpholino) | H | G |
| 99 | O | —CH₂CH₃ | H | —N(CH₃)COCH₃ | H | G |
| 100 | O | —CH₂CH₃ | H | —COOCH₃ | H | G |
| 101 | O | —CH₂CH₃ | H | —N(morpholino) | H | G |
| 102 | NH | CyPr | H | —N(piperazino-CH₃) | H | A |
| 103 | NH | CyPr | H | —N(piperazino-COCH₃) | H | A |
| 104 | NH | CyBu | H | —N(piperazino-COCH₃) | H | A |
| 105 | NH | CyBu | H | H | —N(piperazino-COCH₃) | A |

-continued

| Ex. | X | R¹ | R² | R³ | R⁴ | Method |
|---|---|---|---|---|---|---|
| 106 | NH | CyBu | H | 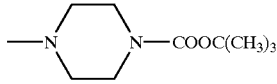 —N(piperazine)N—COOC(CH₃)₃ | H | A |
| 107 | NH | CyBu | H | —SO₂NHCH₂CH₃ | H | F |
| 108 | NH | CyBu | H | —SO₂N(CH₂CH₃)₂ | H | F |
| 109 | NH | CyBu | H | —SO₂N(CH₂)₃CH₃ | H | F |
| 110 | NH | CyBu | H | —SO₂NH(CH₂)₂OH | H | F |
| 111 | NH | CyBu | H | —SO₂NH(CH₂)₄OH | H | F |
| 112 | NH | CyBu | H | —SO₂—N(piperidine) 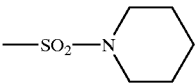 | H | F |
| 113 | NH | CyBu | H | —SO₂—N(piperazine)N—CH₃ 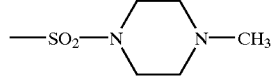 | H | F |
| 114 | NH | CyBu | H | —SO₂NHCH₂COOCH₃ | H | F |
| 115 | NH | CyBu | H | —SO₂NH(CH₂)₃COOCH₂CH₃ | H | F |
| 116 | NH | —CH₂CH₃ | H | —SO₂NH₂ | H | F |
| 117 | NH | —CH₂CH₃ | H | —SO₂NHCH₃ | H | F |
| 118 | NH | —CH₂CH₃ | H | —SO₂N(CH₃)₂ | H | F |
| 119 | NH | —CH₂CH₃ | H | —SO₂N(morpholine) 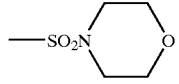 | H | F |
| 120 | NH | —CH₂CH₃ | H | —SO₂—N(piperazine)N—CH₃ 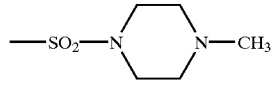 | H | F |
| 121 | NH | CyBu | H | H | H | A |
| 122 | NH | —CH₂CH₃ | H | H | H | A |
| 123 | NH | CyPrCH₂— | H | H | H | A |
| 124 | NH | CyPr | H | —N(2,6-dimethylmorpholine) 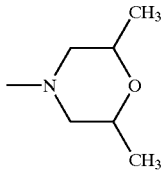 | H | B |
| 125 | NH | —CH₂CH₃ | H | —CONHCH₃ | H | C |
| 126 | NH | —CH₂CH₃ | H | —CONHCH(CH₃)₂ | H | C |
| 127 | NH | —C(CH₃)₃ | H | —N(morpholine) 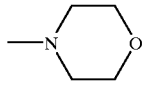 | H | A |
| 128 | NH | —C(CH₃)₃ | H | —COOCH₃ | H | A |
| 129 | NH | CyPr | H | H | —N(piperazine)NCOCH₃ 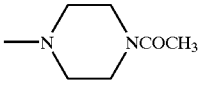 | A |
| 130 | NH | CyBu | H | —CONHCH₃ | H | C |
| 131 | S | —CH₂CH₃ | H | —N(CH₃)COCH₃ | H | C |
| 132 | NH | CyBu | H | —N(piperazine)NCH₃ 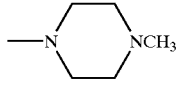 | H | A |

-continued

| Ex. | X | R¹ | R² | R³ | R⁴ | Method |
|---|---|---|---|---|---|---|
| 133 | NH | CyPr | H | H | -N(piperazine)NCH₃ (4-methylpiperazin-1-yl) | A |
| 134 | NH | CyBu | H | H | 4-methylpiperazin-1-yl | A |
| 135 | NH | CyPr | H | H | 4-(tert-butoxycarbonyl)piperazin-1-yl | A |
| 136 | NH | CyBu | H | H | 4-(tert-butoxycarbonyl)piperazin-1-yl | A |
| 137 | S | —CH₂CH₃ | H | —COOCH₃ | H | C |
| 138 | NH | —C(CH₃)₃ | H | —N(CH₃)COCH₃ | H | A |
| 139 | S | —CH(CH₃)₂ | H | morpholin-4-yl | H | C |
| 140 | S | —CH(CH₃)₂ | H | —COOCH₃ | H | C |
| 141 | NH | 6-(1H-indazolyl) | —CH=CH—CH=N— | | H | A |
| 142 | NH | 6-(1H-indazolyl) | H | H | —OCH₃ | A |
| 143 | NH | 6-(1H-indazolyl) | H | —N(CH₃)COCH₃ | H | A |
| 144 | NH | 6-(1H-indazolyl) | H | H | H | A |
| 145 | NH | 5-(1H-indazolyl) | —OCH₃ | H | —OCH₃ | A |
| 146 | NH | 4-(SO₂NH₂)phenyl | H | —N(CH₃)COCH₃ | H | A |
| 147 | NH | 4-(CONH₂)phenyl | —OCH₃ | H | —OCH₃ | A |
| 148 | NH | 6-(1H-indazolyl) | | N-methyl-N-ethyl-2-methylanilino | H | A |

-continued

| Ex. | X | R$^1$ | R$^2$ | R$^3$ | R$^4$ | Method |
|---|---|---|---|---|---|---|
| 149 | NH |  | H | —N(CH$_3$)COCH$_3$ | H | A |
| 150 | NH | 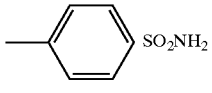 | | 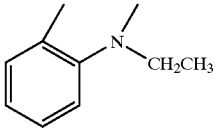 | H | A |
| 151 | NH |  | —OCH$_3$ | —OCH$_3$ | —OCH$_3$ | A |
| 152 | NH | 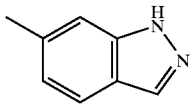 | —OCH$_3$ | H | —OCH$_3$ | A |
| 153 | S | —CH$_2$CH$_3$ | H | 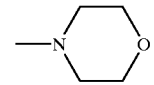 | H | C |
| 154 | NH | —CH$_2$CH$_3$ | | —S—CH=N— | H | C |
| 155 | NH | CyPr | H | 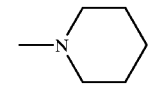 | H | A |
| 156 | NH | —CH$_2$CH$_3$ | | —CH=CH—CH=N— | H | A |
| 157 | NH | CyBu | H | 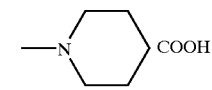 | H | D |
| 158 | NH | CyBu | H | 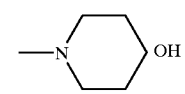 | H | A |
| 159 | NH | CyPr | H | 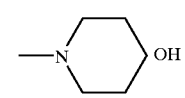 | H | A |
| 160 | NH | CyPr | | —S—CH=N— | H | J |
| 161 | NH | CyBu | | —S—CH=N— | H | J |
| 162 | NH | —C(CH$_3$)$_3$ | | —S—CH=N— | H | J |
| 163 | NH | CyPr | | —O—CH$_2$—CH$_2$—O— | H | J |
| 164 | NH | CyPr | H | 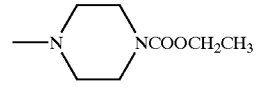 | H | B |
| 165 | NH | CyPr | H | —N(CH$_2$CH$_3$)COCH$_3$ | H | A |
| 166 | NH | —CH$_2$CH$_3$ | H | —N(CH$_2$CH$_3$)COCH$_3$ | H | A |
| 167 | NH | CyBu | H | 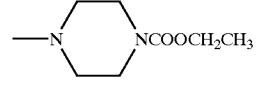 | H | B |
| 168 | NH | —CH$_2$CH$_3$ | H | —NHCOOC(CH$_3$)$_3$ | H | A |
| 169 | NH | —CH$_2$CH$_2$CH$_3$ | H | —NHCOOC(CH$_3$)$_3$ | H | A |
| 170 | NH | —CH(CH$_3$)$_2$ | H | —N(CH$_2$CH$_3$)COCH$_3$ | H | A |
| 171 | NH | —(CH$_2$)$_3$CH$_3$ | H | —N(CH$_2$CH$_3$)COCH$_3$ | H | A |
| 172 | NH | CyPr | H | —N(CH$_3$)COCH$_2$CH$_3$ | H | A |

-continued

| Ex. | X | R¹ | R² | R³ | R⁴ | Method |
|---|---|---|---|---|---|---|
| 173 | NH | —CH₂CH₃ | H | —N(CH₃)COCH₂CH₃ | H | A |
| 174 | NH | —CH(CH₃)₂ | H | —N=CH—S— | | A |
| 175 | NH | —(CH₂)₂CH₃ | H | —N=CH—S— | | A |
| 176 | NH | —CH₃ | H | —SO₂N(CH₃)₂ | H | F |
| 177 | NH | CyPe | H | —SO₂N(CH₃)₂ | H | F |
| 178 | NH | —CH₂CH₃ | H | —SO₂N(CH₂CH₃)₂ | H | F |
| 179 | NH | —CH₂CH₃ | H | —SO₂-piperidinyl | H | F |
| 180 | NH | CyBu | H | piperazinyl-N(CH₂)₂OH | H | B |
| 181 | NH | CyPr | H | piperazinyl-NCH₂COOCH₂CH₃ | H | B |
| 182 | NH | —CH₂CyPr | H | morpholinyl | H | A |
| 183 | NH | —CH(CH₃)₂ | H | morpholinyl | H | A |
| 184 | N(CH₃) | CyPr | H | morpholinyl | H | A |
| 185 | NH | CyPe | H | morpholinyl | H | A |
| 186 | NH | —CH(CH₃)₂ | H | —SO₂N(CH₂CH₃)₂ | H | F |
| 187 | NH | CyPe | H | 2,6-dimethylmorpholinyl | H | A |
| 188 | NH | —CH(CH₃)₂ | H | —SO₂N(CH₃)₂ | H | F |
| 189 | NH | —CH₃ | H | 2,6-dimethylmorpholinyl | H | A |
| 190 | NH | —CH(CH₃)₂ | H | —SO₂-morpholinyl | H | F |

-continued

| Ex. | X | R¹ | R² | R³ | R⁴ | Method |
|---|---|---|---|---|---|---|
| 191 | NH | —(CH₂)₂CH₃ | H | 2,6-dimethylmorpholin-4-yl | H | A |
| 192 | NH | —(CH₂)₃CH₃ | H | —SO₂N(CH₃)₂ | H | F |
| 193 | NH | —CH₃ | H | —SO₂N(CH₂CH₃)₂ | H | F |
| 194 | NH | —CH₃ | H | —SO₂-morpholin-4-yl | H | F |
| 195 | NH | —C(CH₃)₃ | H | 4-acetylpiperazin-1-yl | H | A |
| 196 | NH | —(CH₂)₂CH₃ | H | —SO₂N(CH₃)₂ | H | F |
| 197 | NH | CyBu | H | —COOCH₂CH₃ | H | A |
| 198 | NH | —C(CH₃)₃ | H | H | H | A |
| 199 | NH | —C(CH₃)₃ | H | —O—CH₂—CH₂—O— | | A |
| 200 | NH | —CH₂CyPr | H | —CH₂—O—CO— | | A |
| 201 | NH | —C(CH₃)₃ | H | —CH₂—O—CO— | | A |
| 202 | NH | CyPe | H | —CH₂—O—CO— | | A |
| 203 | NH | CyPr | H | —COOCH₂CH₃ | H | A |
| 204 | NH | —CH₂CH₂-C₆H₄-OH | H | —N(CH₃)COCH₃ | H | A |
| 205 | NH | —C(CH₃)₃ | H | —N(CH₂CH₃)COCH₃ | H | A |
| 206 | NH | —CH₂CyPr | H | —N=CH—S— | | A |
| 207 | NH | —CH₂CyPr | H | 4-hydroxypiperidin-1-yl | H | A |
| 208 | NH | —CH(CH₃)₂ | H | 4-hydroxypiperidin-1-yl | H | A |
| 209 | NH | CyBu | H | —N(COCH₃)—CH₂—CH₂— | | A |
| 210 | NH | —(CH₂)₂-C₆H₄-SO₂NH₂ | H | —N(CH₃)COCH₃ | H | A |
| 211 | NH | CyBu | H | —COOCH(CH₃)₂ | H | I |
| 212 | NH | CyBu | H | 3,3-dimethyl-2-oxoazetidin-1-yl | H | A |
| 213 | NH | CyPr | H | 3,3-dimethyl-2-oxoazetidin-1-yl | H | A |
| 214 | NH | —CH(CH₃)₂ | H | —N(CH₃)COCH₂CH₃ | H | A |
| 215 | NH | —(CH₂)₂CH₃ | H | —N(CH₃)COCH₂CH₃ | H | A |

-continued

| Ex. | X | R¹ | R² | R³ | R⁴ | Method |
|---|---|---|---|---|---|---|
| 216 | NH | CyPr | H | pyrrolidinone (N-linked, C=O adjacent) | H | A |
| 217 | NH | CyPr | H | —NHCOOCH₃ | H | A |
| 218 | NH | —C(CH₃)₃ | H | pyrrolidinone (N-linked, C=O adjacent) | H | A |
| 219 | NH | CyBu | H | —N(piperazine)NCH₂CH₃ | H | B |
| 220 | NH | CyBu | H | —N(CH₃)COCH₃ | H | A |
| 221 | NH | CyPe | H | —N(piperazine)N-COOC(CH₃)₃ | H | A |

The preparations of certain of the above Examples are described in more detail below:
Abbreviations use are as follows:
NMP: N-methylpyrrolidone
DCM: dichloromethane
THF: tetrahydrofuran
PyBOP: benzotriazol-1-yloxy-tris-pyrrolidino-phosphonium hexafluorophosphate
DMAP: N,N-dimethyl-4aminopyridine
DMF: dimethyl formamide
HPLC: high performance liquid chromatography
TLC: thin layer chromatography Example 5 a. Cyclopropylamine (6.65 g, 0.116M) and N,N-dfisopropylethylamine (20.8 ml, 0.116M) is added to a suspension of 2,6-dichloropurine (20 g, 0.106M) in n-butanol (200 ml). The mixture is stirred at 60° C. for 20 hours. The mixture is cooled and the precipitate isolated by filtration, washed with n-butanol and dried under vacuum to give 6-cyclopropylamino-2-chloropurine; ES+ (M+1) 209.5; mp 249.7° C. dec.

b. A solution of 6-cyclopropylamino-2-chloropurine (0.535 g, 2.5 mmol) and 4-morpholinoaniline (0.683 g, 3.8 mmol) in NMP(2.5 ml) is stirred at 130° C. After the solid has dissolved, N,N-diisopropylethylamine (0.65 ml, 3.8 mmol) is added and the mixture stirred at 130° C. for 48 hours. The mixture is cooled and partitioned between ethyl acetate and water. The layers are separated and the aqueous layer extracted with ethyl acetate (2×100 ml). The combined organics are evaporated and the residue purified by silica column chromatography (4%Methanol:DCM). The product is isolated as a brown solid which is dried under vacuum; ES+ (M+1) 352; mp 201.9–203.7° C.

Example 6 a. Cyclobutylamine (20 g, 0.28M) and N,N-diisopropylethylamine (50.4 ml, 0.28M) is added to a suspension of 2,6-dichloropurine (48.4 g, 0.25M) in n-butanol (480 ml). The mixture is stirred at 60° C. for 20 hours. The mnixture is cooled and the precipitate isolated by filtration, washed with n-butanol and dried under vacuum to give 6cyclobutylamino-2-chloropurine;ES+ (M−1) 222.5; mp 237.8° C. dec.

b. A solution of 6-cyclobutylamino-2-chloropurine (100 mg, 0.447 mmol), 4-amino-N-methylacetanilide(220 mg, 1.34 mmol) in NMP(1 ml) is stirred at 145° C., under argon. After 7 hours the solvent is removed by evaporation, the residue suspended in methanol and the suspension ultrasonicated for 3 minutes. The solid is separated by filtration, washed with cold methanol and dried under vacuum; ES− (M−1) 350; mp 314–318° C.

Example 19 a. A solution of 6-cyclopropylamino-2-chloropurine (5a) (0.209 g, 1 mmol) and methyl 4-aminobenzoate (0.377 g, 2.5 mmol) in NMP (2 ml) is stirred at 130° C., for 16 hours. The mixture is diluted with water and treated with 4N sodium hydroxide to achieve pH14. The solution is extracted with ethyl acetate (4×100 ml). The combined organics are washed with water, dried(MgSO₄), filtered and evaporated. The residue is purified further by silica column chromatography, to yield a colourless oil; ES+ (M+1) 325.3.

Example 34 a. To a stirred ethereal solution of N-methylcyclopropylamine (50 ml), is added 2,6-dichloropurine(1.3 g, 6.8 mmol). After 15 minutes n-butanol(3 ml) is added and the suspension ultrasonicated at 40° C. for 1 hour. A further aliquot of n-butanol is added and the ultrasonication continued for 2.5 hours. The mixture is stirred at ambient temperature for 16 hours. The precipitate isolated by filtration, washed with ether/methanol and dried under vacuum at 115° C. to give 6-N-methylcyclopropylamino-2-chloropurine; ES+ (M+1) 223.5; mp 234–235° C. dec.

b. To a hot solution of 6-N-methylcyclopropylamino-2-chloropurine (0.2 g, 0.89 mmol) in NMP(1.7 ml), is added N-aminoindazole (0.26 g, 1.96 mmol) and conc. hydrochloric acid (7.7 ml). The mixture is stirred at 107° C., for 20 hours and stirred at ambient temperature for 48 hours. The solvent is removed by evaporation and the residue triterated with methanol. The solid is isolated by filtration,washed with methanol and dried under vacuum, at 100° C. The solid is purified further by silica gel chromatography, and crystallised from methanol; ES+ (M+1) 321.3; mp 289–292° C.

Example 75 a. A solution of 6-cyclobutylamino-2-chloropurine(6a) (5 g, 22.35 mmol) and aniline (6.1 ml, 67 mmol) in NMP (25 ml) is heated at 150° C., for 6 hours and allowed to cool. Upon standing at ambient temperature for 16 hours, the resulting crystals are isolated by filtration, washed with dioxane(50 ml) and dried to give 6cyclobutylamino-2-anilinopurine; ES+ (M+1) 280.86; mp 312–314° C.

b. 6-Cyclobutylamino-2-anilinopurine (200 mg, 0.631 mmol) is added cautiously to chlorosulfonic acid (2 ml). The solution is stired at 50° C., for 2 hours. After cooling to ambient temperature, the mixture is added dropwise to ice/water(20 ml). The precipitate is filtered and washed with cold water (5 ml). The solid, 6-cyclobutylamino-2-(4-chlorosulfonylanilino)purine, is dissolved in NMP (2 ml).

c. To a 1M solution of methylamine in ethanol(1 ml), is added 400 μl of the solution of 6-cyclobutylamino-2-(4-chlorosulfonylanilino)purine in NMP. After 2 hours, the solvent is removed and the residue purified using preparative HPLC; ES+ (M+1) 374.4.

Example 79 a. To a suspension of 2,6-dichloropurine (2 g, 10.6 mmol) in n-butanol (3 ml), is added ethylamine (2M in THF)(15 ml). The solution is stirred at 84° C. for 2.5 hours and then cooled to ambient and stirred for a further 2 hours. The resulting precipitate is isolated by filtration, washed with n-butanol, methanol and ethyl acetate. The solid is dried at 70° C., under vacuum, for 16 hours to give 6-ethylamino-2-chloropurine; ES+ (M+1)197.5,198.2; mp 237–239° C.

b. A solution of 6-ethylamino-2-chloropurine (200 mg, lmmol), methyl-4-aminobenzoate (382 mg, 2.5 mmol) in NMP(0.77 ml) is stirred at 123° C., under argon. After 22 hours the solvent is removed by evaporation, the residue suspended in methanol and the suspension ultrasonicated for 3 minutes. The solid is separated by filtration, washed with cold methanol and dried under vacuum, prior to further purification by silica column chromatography. The product is crystallised from methanol to give 6-ethylamino-2-(methyl-4-aminobenzoate)purine; ES+ (M+1) 312.84; mp 229–230° C.

c. To a suspension of 6-cthylamino-2-(methyl-4-aminobenzoate)purine (0.7 g, 2 mmol) in THF/water(1:1) (55 ml), is added a solution of lithium hydroxide monohydrate (1.1 g, 26 mmol) in water (17 ml). The mixture is stirred at 55° C. for 48 hours. The solvent is removed by evaporation and the residue ultrasonicated in water. The solid is removed by filtration and the filtrate neutralised with conc. hydrochloric acid. The precipitate is isolated by filtration, washed with water and dried under vacuum, at 75° C.; ES+ (M+1) 398.71; mp 301–303° C. dec.

Example 80

To a solution of 6-ethylamino-2-(methyl-4-aminobenzoic acid)purine (79 c)(50 mg, 0.1493 mmol) in DMF(1 ml), stirring at 45° C., is added DMAP(20 mg) and 2M ethylamine in THF(0.5 ml). The mixture is cooled to 25° C. and PyBOP (78 mg) added. The mixture is stirred at ambient temperature for 20 hours, prior to the removal of solvent. The residue is suspended in water and ultrasonicated for 2 minutes. The mixture is acidified to pH4 with the addition of 1N hydrochloric acid. The product is isolated by filtration, washed with water and dried under vacuum. The product can be further purified using preparative TLC, to yield a crystalline solid; ES+ (M+1) 325; mp 295° C. dec.

Example 89

A mixture of 10 ml of the suspension of 6-ethylamino-2-(methyl-4-aminobenzoyl chloride)purine in benzene prepared in Example 94a and dimethylamine (33% solution in methanol)(2 ml) is ultrasonicated for 40 minutes. and stirred at ambient temperature for 48 hours. The solvent is removed in vacuo and the residue suspended in water. The water is decanted and the oily residue purified by preparative HPLC. The product is crystallised from hot methanol and dried under vacum at 70° C.; ES+ (M+1) 325.64; mp 262–264° C. dec.

Example 94 a. A suspension of 6-ethylamino-2-(methyl4-aminobenzoic acid)purine(79 c)(150 mg, 0.502 mmol) in thionyl chloride(12 ml) is agitated by the bubbling through of argon at ambient temperature for 16 hours. A further portion of thionyl chloride (5 ml) is added and the reaction continued for 20 hours. The residue, 6-ethylamino-2-(methyl-4-aminobenzoyl chloride)purine, is suspended in benzene (20 ml).

b. To 10 ml of the suspension of 6-ethylamino-2-(methyl4-aminobenzoyl chloride)purine in benzene, is added iso-propanol (1.5 ml)and triethylamine (0.2 ml). The mixture is ultrasonicated for 30 minutes and stirred at ambient temperature for 48 hours. The solvent is removed in vacuo and the residue heated with water. The resultant crystalline solid is isolated by filtration and washed with water. It is purified further by preparative HPLC, to yield a colourless solid; ES–(M–1) 340.

Example 96 a. Sodium metal (1.53 g, 0.067M) is dissolved in a mixture of cyclobutanol (8 g, 0.11M) and dry THF (20 ml), at 90° C., under nitrogen, for 4 hours. The mixture is cooled to 0° C. and 2,6-dichloropurine (4.39 g, 0.024M) added. The mixture is stirred at ambient temperature for 0.5 hours, prior to the addition of glacial acetic acid (10 ml) and water (30 ml). The precipitate is isolated by fitration, washed with water and dried under vacuum to yield a colourless solid, 6-cyclobutylether-2-chloropurine; ES+ (M+1) 224.74; mp 247.6–249.7° C. dec.

b. To a suspension of 6-cyclobutylether-2-chloropurine (0.22 g, 0.98 mmol) in NMP(2 ml), is added silver triflate (0.252 g, 0.98 mmol). The mixture is heated to 120° C. to achieve dissolution. To this solution is added 4amino-N-methyl acetanilide (0.402 g, 2.4mol) and the mixture stirred at 120° C., for 16 hours. The mixture is cooled and water (10 ml) and ethyl acetate(20 ml) added. The phases are separated and the aqueous phase extracted with ethyl acetate(2×30 ml). The combined organics are washed with water (30 ml), saturated brine (50 ml), dried (MgSO$_4$), filtered and evaporated. The residue is purified further by silica column chromatography; ES+ (M+1) 352.72.

Example 131 a. To a solution of ethanethiol (0.93 ml, 12.5 mmol) in dry THF(8 ml), is added sodium hydride (0.48 g, 12.5 mmol).

Once the effervesence has subsided, 2,6-dichloropurine (0.945 g, 5 mmol) is added. The mixture is stirred at ambient temperature, under nitrogen for 1.5 hours and then heated to reflux for 2 hours. The mixture is cooled, the solvent removed by evaporation and purified by silica column chromatography, to yield 6-ethanemercapto-2-chloropurine; ES+ (M+1) 215.3, 217.2; mp 262–263° C.

b. A solution of 6-ethanemercapto-2-chloropurine (107 mg, 0.5 mmol) and 4-amino-N-methylacetanilide (246 mg, 1.5 mmol) in NMP (0.5 ml), is heated at 140° C., for 17 hours. The cooled mixture is poured into water and extracted with ethyl acetate (3×50 ml). The combined organics are dried(MgSO$_4$), filtered and evaporated. The residue is purified by silica column chromatography, to yield a colourless crystalline product; ES+ (M+1) 342.76/343.46; mp 219–220° C.

Example 220

The product of Example 6 (500 mg, 1.42 mmol) is slurried in a mixture of dichloromethane (5 ml) and water (5 ml). Aqueous 4N sodium hydroxide is added to adjust the aqueous layer to pH 10. The organic layer is discarded and the aqueous layer is extracted with ethyl acetate. The solvent is removed to give a solid which is slurried in dichloromethane, filtered and dried; to yield a colourless solid. HPLC retention time 2.669 min (Hewlett Packard Chemstation at λ=254 nm, Phenomenex Luna C8 50 mm×0.2 mm column, pore size 3 μm, at 50° C.; A=citrate-phosphate buffer pH3; B=acetonitrile; gradient 0 to 95% B in 3 minutes at 0.7 ml/min.

The other Examples are prepared analogously to the respective detailed Example above appropriate for the synthetic method (A to J) shown in the above table.

Characterising mass spectrometry and melting point data for the above Examples are shown, together with details of the salt-forming acid where the Example is a salt, in the following table:

| Ex | Acid | ES+/ES− | MP° C. |
|---|---|---|---|
| 1 | HCl | MH + 307 | 302–305 |
| 2 | — | MH + 307 | 315–317 |
| 3 | — | MH + 382 | — |
| 4 | — | MH + 295.4 | 329–330 |
| 5 | — | MH + 352 | 201.9–203.7 |
| 6 | HCl | MH − 350 | 314–318 |
| 7 | — | MH + 321 | 289–291 |
| 8 | — | MH + 321 | 322–324 |
| 9 | — | MH − 350 | 231.8–232.5 |
| 10 | — | MH + 325.6 | 300–302 |
| 11 | HCl | MH + 352 | 198.7–199.8 |
| 12 | HCl | MH + 320.7 | 380 dec |
| 13 | — | MH + 327.6 | — |
| 14 | — | M − H320.5 | 265–271 |
| 15 | — | MH + 323.2 | 198–220 dec |
| 16 | — | MH + 321.3 | 319–321 |
| 17 | — | MH + 352.2 | 305–308 |
| 18 | — | MH − 320.3 | 248 dec |
| 19 | — | MH + 325.3 | 164.5–169.1 |
| 20 | — | MH − 364 | 124.3–128.5 |
| 21 | HCl | MH + 335.0 | 350–355 |
| 22 | — | MH + 321.2 | 182–185 |
| 23 | — | MH + 396 | 182–185 |
| 24 | HCl | MH + 307 | 292–296 |
| 25 | — | MH + 320.7 | 292–296 |
| 26 | — | MH + 339 | 105.5–110.3 |
| 27 | HCl | MH + 267.2 M − H265.1 | 253–254 |
| 28 | HCl | MH + 340 | 303–305 |
| 29 | — | MH + 353 | 161.9–162.6 |
| 30 | HCl | MH + 353 | 216.8–219.4 |
| 31 | HCl | MH + 342 | 287–289 |
| 32 | HCl | MH + 356 | 302–305 |
| 33 | HCl | M − H336 | 316–319 |
| 34 | — | MH + 321.3 | 289–292 |
| 35 | — | MH + 352.4 | 280–282 |
| 36 | — | MH + 366.2 | 271–273 |
| 37 | — | MH + 353 | 161.9–162.6 |
| 38 | — | MH + 353 | 216.8–219.4 |
| 39 | HCl | MH + 460 | 297–299 |
| 40 | — | MH + 325.6 | 314–317 |
| 41 | — | MH + 297.1 | — |
| 42 | — | M − H307.9 | 214–216 |
| 43 | HCl | — | 337–339 |
| 44 | — | MH + 327.2 | — |
| 45 | HCl | MH + 346.2 | 250–300 |
| 46 | — | MH + 396 | — |
| 47 | — | MH + 339.67 | 225–228 |
| 48 | HCl | MH + 325 | 280 dec |
| 49 | — | MH + 367 | 193.2–195.0 |
| 50 | — | MH + 394 | 148–150 |
| 51 | HCl | MH + 310.7 | 307–310 |
| 52 | — | MH + 339 | 189.6–192.4 |
| 53 | HCl | MH + 298.8 | 304–307 |
| 54 | HCl | MH + 357.3 | 251–252 |
| 55 | — | MH + 324.7 | 127–130 |
| 56 | — | MH + 353 | 113.2–115.7 |
| 57 | HCl | MH + 325 | 284–286 |
| 58 | HCl | M − H337 | 290 dec |
| 59 | — | M − H406 | 136.3–138.4 |
| 60 | HCl | M − H469.4 | 245–251 |
| 61 | HCl | MH + 325 | 350 dec |
| 62 | — | MH + 399.8 | — |
| 63 | — | MH + 403.1 | 179–183 |
| 64 | — | MH + 464 | — |
| 65 | HCl | MH + 281 | — |
| 66 | — | M − H379.98 | 225–230 |
| 67 | HCl | MH + 212.2 | 294–297 |
| 68 | — | MH + 410.07 | 253–255 |
| 69 | HCl | MH + 378.8 | 231–233 |
| 70 | HCl | MH + 340.17 | 317–321 |
| 71 | HCl | MH + 326.2 | 318–322 |
| 72 | — | MH + 396.14 | 240–241 |
| 73 | — | MH + 312.71 | 229–230 |
| 74 | CF$_3$CO$_2$H | MH + 360.4 | — |
| 75 | CF$_3$CO$_2$H | MH + 374.4 | — |
| 76 | CF$_3$CO$_2$H | MH + 388.4 | — |
| 77 | CF$_3$CO$_2$H | MH + 430.4 | — |
| 78 | CF$_3$CO$_2$H | MH + 418.4 | — |
| 79 | — | MH + 398.71 | 301–303 |
| 80 | — | MH + 325 | 295 dec |
| 81 | — | M − H322 | 227.6–229.3 |
| 82 | — | M − H322 | 228.9–230.2 |
| 83 | — | M − H336 | 214.3–216.7 |
| 84 | — | MH + 339.7 | 291 dec |
| 85 | — | MH + 353.67 | 307 dec |
| 86 | — | MH + 353.62 | 286 dec |
| 87 | — | MH + 367.84 | 295 dec |
| 88 | — | MH + 377.61 | 258–261 dec |
| 89 | CF$_3$CO$_2$H | MH + 325.64 | 262–264 dec |
| 90 | HCl | MH + 365.74 | 295–298 |
| 91 | — | MH + 449 | 226.7–228.4 |
| 92 | — | MH − 309 | 278.2–280.1 |
| 93 | — | MH − 323 | — |
| 94 | CF$_3$CO$_2$H | M − H340 | — |
| 95 | — | MH + 365.78 | 243–245 |
| 96 | — | MH + 352.72 | — |
| 97 | — | MH + 339.68 | — |
| 98 | — | MH + 366.80 | — |
| 99 | — | MH + 326.80 | — |
| 100 | — | MH + 313.75 | — |
| 101 | — | MH + 340.51 | — |
| 102 | — | MH − 363 | — |
| 103 | — | MH − 391 | — |
| 104 | — | MH − 405 | — |
| 105 | — | MH − 405 | — |

-continued

| Ex | Acid | ES+/ES− | MP° C. |
|---|---|---|---|
| 106 | — | MH − 463 | — |
| 107 | — | MH + 387.83 | 257 dec |
| 108 | — | MH + 415.64 | 263 dec |
| 109 | — | MH + 415.69 | 278 dec |
| 110 | — | MH + 403.66 | 242 dec |
| 111 | — | MH + 431.79 | 231 dec |
| 112 | — | MH + 427.76 | 255 dec |
| 113 | CF$_3$CO$_2$H | MH + 442.69 | 250 dec |
| 114 | — | MH + 431.57 | 240 dec |
| 115 | — | MH + 473.67 | 237 dec |
| 116 | — | MH + 333.59 | 267 dec |
| 117 | — | MH + 347.53 | 260 dec |
| 118 | — | MH + 361.78 | 231 dec |
| 119 | — | MH + 403.72 | 252 dec |
| 120 | — | MH + 416.69 | 246 dec |
| 121 | — | MH + 280.86 | 312–314 |
| 122 | — | MH + 254.69 | 305–306 |
| 123 | — | MH + 280.76 | 304–306 |
| 124 | — | MH + 379.56 | 212–214 dec |
| 125 | — | MH + 312.5 | >250 |
| 126 | — | M − 1338.5 | 243–244 |
| 127 | — | MH + 368.1 | 227–229 |
| 128 | — | MH + 341.5 | 163–165 |
| 129 | — | MH − 391 | — |
| 130 | — | MH − 337 | 256.4–257.6 |
| 131 | — | MH + 342.76/343.46 | 219–220 |
| 132 | — | MH − 377 | — |
| 133 | — | MH − 363 | — |
| 134 | — | MH − 377 | — |
| 135 | — | MH + 451 | — |
| 136 | — | MH + 465 | — |
| 137 | — | MH + 330.5 | 196–199 |
| 138 | — | MH + 354.5 | 273–274 |
| 139 | — | MH + 371.5 | 138–140 |
| 140 | — | MH + 344.4 | 224–226 |
| 141 | — | MH + 393.7 | 327–332 |
| 142 | HCl | MH + 373.35 | 348–351 |
| 143 | — | MH + 414.2 | — |
| 144 | HCl | MH + 343.26 | 380–388 |
| 145 | — | MH + 403.3 | 331–334 |
| 146 | — | MH + 453.1 | — |
| 147 | — | MH + 406.3 | — |
| 148 | — | MH + 460.1 | — |
| 149 | — | MH + 445.3 | — |
| 150 | — | MH + 499.1 | — |
| 151 | — | MH + 436.8 | — |
| 152 | — | MH + 403.3 | 179–183 |

| Ex | Add | Mass Method | M+/M− | MP ° C. |
|---|---|---|---|---|
| 153 | — | AP+ | MH+ 357.5 | 115–116 |
| 154 | — | AP+ | MH+ 312.8 | 222–224 |
| 155 | — | ES+ | MH+ 350 | 168.4–169.2 |
| 156 | — | AP+ | MH+ 306.5 | 254–256 |
| 157 | — | ES+ | MH+ 408 | >300 |
| 158 | — | ES+ | MH+ 380 | 248.8–250.9 |
| 159 | — | ES+ | MH+ 366 | 244.4–245.2 |
| 160 | — | AP+ | MH+ 324.4 | — |
| 161 | — | AP+ | MH+ 338.4 | — |
| 162 | — | AP+ | MH+ 340.5 | — |
| 163 | — | AP+ | MH+ 325.5 | — |
| 164 | — | ES+ | MH+ 422.79 | 162–165 |
| 165 | — | ES+ | MH+ 351.85 | — |
| 166 | — | ES+ | MH+ 365.76 | — |
| 167 | — | ES+ | MH+ 436.88 | — |
| 168 | — | TOF ES+ | MH− 368.2 | — |
| 169 | — | TOF ES+ | MH− 382.2 | — |
| 170 | — | TOF ES+ | MH+ 354.2 | — |
| 171 | — | TOF ES+ | MH+ 366.2 | — |
| 172 | — | TOF ES+ | MH+ 352.8 | — |
| 173 | — | TOF ES+ | MH+ 340.14 | — |
| 174 | — | TOF ES+ | MH+ 326.7 | — |
| 175 | — | TOF ES+ | MH+ 326.8 | — |
| 176 | CF$_3$COOH | TOF ES+ | MH+ 347.78 | 264–267 |
| 177 | CF$_3$COOH | ES+ | MH+ 402.19 | 242–243 |
| 178 | CF$_3$COOH | ES+ | MH+ 389.82 | 248–250 |
| 179 | CF$_3$COOH | ES+ | MH+ 401.89 | 250–252 |
| 180 | CF$_3$COOH | ES+ | MH+ 408.79 | 143–144 dec |
| 181 | CF$_3$COOH | ES+ | MH+ 436.86 | 146–148 dec |
| 182 | — | TOF ES+ | MH+ 366 | — |
| 183 | — | TOF ES+ | MH+ 354 | — |
| 184 | — | TOF ES+ | MH+ 366 | — |
| 185 | — | TOF ES+ | MH+ 380 | — |
| 186 | CF$_3$COOH | AP+ | MH+ 404.5 | 267–268 |
| 187 | — | TOF ES+ | MH+ 408 | — |
| 188 | CF$_3$COOH | AP− | M− 376.4 | 261–262 |
| 189 | — | TOF ES+ | MH+ 354 | — |
| 190 | CF$_3$COOH | AP+ | MH+ 416.3 | 245–247 |
| 191 | — | TOF ES+ | MH+ 382 | — |
| 192 | CF$_3$COOH | AP+ | MH+ 390.3 | 259–260 |
| 193 | CF$_3$COOH | ES+ | MH+ 376.14 | 267–268 |
| 194 | CF$_3$COOH | ES+ | MH+ 388.11 | 249–252 |
| 195 | — | TOF ES+ | MH+ 408.99 | — |
| 196 | CF$_3$COOH | ES+ | MH+ 375.74 | 245–246 |
| 197 | CF$_3$COOH | ES+ | MH+ 352.78 | — |
| 198 | CF$_3$COOH | TOF ES+ | MH+ 283.11 | >280 |
| 199 | — | TOF ES+ | MH+ 341.22 | — |
| 200 | — | TOF ES+ | MH+ 337.17 | — |
| 201 | — | TOF ES+ | MH+ 339.16 | — |
| 202 | — | TOF ES+ | MH+ 351.19 | — |
| 203 | CF$_3$COOH | TOF ES+ | MH+ 339.12 | — |
| 204 | CF$_3$COOH | TOF ES+ | MH+ 418.11 | — |
| 205 | — | TOF ES+ | MH+ 368.15 | — |
| 206 | — | TOF ES+ | MH+ 338.07 | — |
| 207 | — | TOF ES+ | MH+ 380.19 | — |
| 208 | — | TOF ES+ | MH+ 368.18 | — |
| 209 | — | AP+ | MH+ 364.5 | — |
| 210 | CF$_3$COOH | TOF ES+ | MH+ 481.03 | 242–243 |
| 211 | CF$_3$COOH | ES+ | MH+ 366.9 | 258–259 |
| 212 | CF$_3$COOH | ES+ | MH+ 378 | >285 |
| 213 | CF$_3$COOH | ES+ | MH+ 363.8 | — |
| 214 | CF$_3$COOH | TOF ES+ | MH+ 354.8 | 103.5–105.8 |
| 215 | CF$_3$COOH | — | — | 129.3–131.4 |
| 216 | HCl | ES+ | MH+ 349.9 | 280–283 |
| 217 | — | — | — | — |
| 218 | — | — | — | — |
| 219 | CF$_3$COOH | ES+ | MH+ 392.93 | 184–186 dec |
| 220 | — | | | |
| 221 | — | TOF ES+ | MH+ 479.22 | |

What is claimed is:
1. A compound of formula

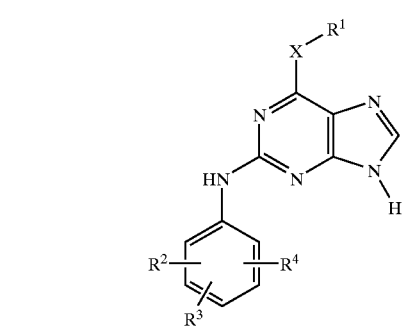

in free or salt form, wherein
X is an oxygen or sulfur atom or a group NR$^5$,
R$^1$ is an alkyl, alkenyl, cycloalkyl, benzocycloalkyl, cycloalkylalkyl or aralkyl group which optionally may be substituted by hydroxy, alkoxy, carboxy or alkoxycarbonyl or, when X is $NR^5$, $R^1$ may alternatively be a group of formula

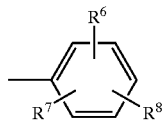

II or a monovalent heterocyclic radical having up to 20 carbon atoms and one, two, three, or four heteroatoms selected from nitrogen, oxygen, and sulfur, the radical optionally having an alkyl, alkylcarbonyl, hydroxyalkyl, alkoxyalkyl, or aralkyl group attached to a ring carbon or nitrogen atom and being linked to the remainder of the molecule through a ring carbon atom, $R^2$, $R^3$, $R^4$, $R^6$, $R^7$, and $R^8$ are each independently hydrogen, halogen, alkyl, haloalkyl, alkoxy, carboxy, alkoxycarbonyl, carboxyalkyl, alkoxycarbonylalkyl, $-N(R^9)R^{10}$, $-SO_2N(R^{11})R^{12}$, $C_1-C_4$-alkylene-$SO_2N(R^{11})R^{12}$ or $-CON(R^{13})R^{14}$ or, when two of $R^2$, $R^3$ and $R^4$, or two of $R^6$, $R^7$ and $R^8$, are attached to adjacent carbon atoms on the indicated benzene rings, they denote, together with the carbon atoms to which they are attached, a carbocyclic group having 5 to 10 ring atoms or a heterocyclic group having 5 to 10 ring atoms of which one, two or three are hetero atoms selected from nitrogen, oxygen and sulfur, $R^5$ is hydrogen or alkyl, $R^9$ is hydrogen or alkyl and $R^{10}$ is hydrogen, alkyl or $-COR^{15}$ where $R^{15}$ is alkyl, haloalkyl, alkoxy, alkoxyalkyl, alkoxycarbonyl, carboxyalkyl or alkoxycarbonylalkyl, or $R^9$ and $R^{10}$, together with the nitrogen atom to which they are attached, denote a heterocyclic group having 5 or 6 ring atoms of which one or two are hetero atoms selected from nitrogen, oxygen and sulfur, $R^{11}$ is hydrogen or alkyl and $R^{12}$ is hydrogen, alkyl, hydroxyalkyl, alkoxyalkyl, carboxyalkyl or alkoxycarbonylalkyl, or $R^{11}$ and $R^{12}$ together with the nitrogen atom to which they are attached denote a heterocyclic group having 5 or 6 ring atoms of which one or two are hetero atoms selected from nitrogen, oxygen and sulfur, and when $R^9$ and $R^{10}$, or $R^{11}$ and $R^{12}$, together with the nitrogen atom to which they are attached, denote a heterocyclic group having two nitrogen atoms in the ring, said group may be optionally substituted on the second nitrogen atom by a $C_1-C_4$-alkyl, hydroxy-$C_1-C_4$-alkyl, $C_1-C_4$-alkylcarbonyl, a $C_1-C_4$-alkoxycarbonyl, or phenyl-$C_1-C_4$-alkyl group, and when $R^9$ and $R^{10}$, or $R^{11}$ and $R^{12}$, together with the nitrogen atom to which they are attached, denote a heterocyclic group having one nitrogen atom and one oxygen atom in the ring, said group may be optionally substituted on one or more ring carbon atoms by a $C_1-C_4$-alkyl group, and $R^{13}$ and $R^{14}$ are each independently hydrogen or alkyl; with the exception of 2-(p-n-butylanilino)-6-methoxypurine, 2-(p-n-butylanilino)-6-(methylthio) purine, 2,6-di(phenylamino)purine, 2,6-di(p-tolylamino)purine, and 2-(p-tolylamino)-6-(phenylamino)purine.

2. A compound of claim 1 wherein said monovalent heterocyclic radical is pyrryl, pyridyl, piperidyl, furyl, tetrahydrofuryl, or thienyl, imidazolyl, pyrimidinyl, piperazinyl, oxazolyl, isoxazolyl, thiazolyl, morpholinyl, or thiomorpholinyl, optionally having an alkyl, alkylcarbonyl, hydroxyalkyl, alkoxyalkyl, or aralkyl group attached to a ring carbon or nitrogen atom and being linked to the remainder of the molecule through a ring carbon atom.

3. A compound of claim 1, wherein said heterocyclic group is pyrrolidinyl, imidazolyl, imidazolidinyl, piperidyl, or piperazinyl, optionally substituted on the second nitrogen atom by a $C_1-C_4$-alkyl, hydroxy-$C_1-C_4$-alkyl, $C_1-C_4$-alkylcarbonyl, $C_1-C_4$-alkoxycarbonyl, or phenyl-$C_1-C_4$-alkyl group, or said heterocyclic group is a tetrahydro-oxazolyl, tetrahydro-isoxazolyl or morpholino group optionally substituted on one or more ring carbon atoms by a $C_1-C_4$-alkyl group.

4. A compound of claim 1, which is a compound of formula

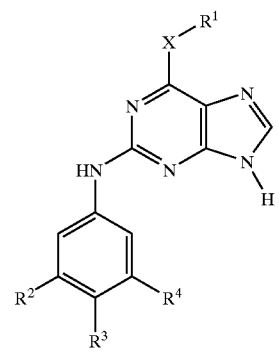

III in free or salt form, wherein
$R^1$ is a group of formula

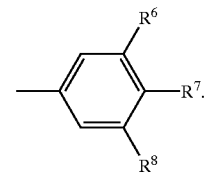

IV

5. A compound of claim 1, in which $R^1$ is a $C_1-C_{10}$-alkyl, $C_2-C_{10}$-alkenyl, $C_3-C_{10}$-cycloalkyl, benzo-$C_3-C_{10}$-cycloalkyl, phenyl-$C_1-C_{10}$-alkyl or $C_3-C_{10}$-cycloalkyl-$C_1-C_4$-alkyl group which optionally substituted by a hydroxy, carboxy or $C_1-C_4$-alkoxycarbonyl group, or $R^1$ is a heterocyclyl radical having 5 or 6 ring atoms and one or two nitrogen atoms, or one nitrogen atom and one oxygen atom, in the ring and optionally substituted on a ring nitrogen atom by $C_1-C_4$-alkyl, hydroxy-$C_1-C_4$-alkyl, $C_1-C_4$-alkylcarbohyl or phenyl-$C_1-C_4$-alkyl, or $R^1$ is a group of formula II or formula IV respectively in which one of $R^6$, $R^7$ and $R^8$ is hydrogen, $C_1-C_4$-alkyl or $C_1-C_4$-alkoxy, and (i) the second and third of $R^6$, $R^7$ and $R^8$ are each independently hydrogen, $C_1-C_4$-alkyl or $C_1-C_4$-alkoxy or (ii) the second of $R^6$, $R^7$ and $R^8$ is hydrogen and the $R^6$, $R^7$ and $R^8$ is carboxy, $C_1-C_{10}$-alkoxycarbonyl, carboxy $C_1-C_{10}$-alkyl, $C_1-C_{10}$-alkoxycarbonyl-$C_1-C_{10}$-alkyl, $-N(R^9)R^{10}$, $-SO_2N(R^{11})R^{12}$, $C_1-C_4$-alkylene-$SO_2N(R^{11})R^{12}$ or $-CON(R^{13})R^{14}$, or (iii) the second and third of $R^6$, $R^7$ and $R^8$ are attached to adjacent carbon atoms in the indicated benzene ring and, together with said adjacent carbon atoms, denote a carbocyclic group having 5 or 6 ring atoms or a monocyclic heterocyclic group having 5 or 6 ring atoms and one or two nitrogen atoms in the ring, one of $R^2$, $R^3$ and $R^4$ is hydrogen, $C_1$–$C_4$-alkyl or $C_1$–$C_4$-alkoxy and (a) the second and third of $R^2$, $R^3$, and $R^4$ are each independently hydrogen, $C_1$–$C_4$-alkyl or $C_1$–$C_4$-alkoxy, or (b) the second of $R^2$, $R^3$, and $R^4$ is hydrogen and the third of $R^2$, $R^3$, and $R^4$ is carboxy, $C_1$–$C_{10}$-alkoxycarbonyl, carboxy-$C_1$–$C_{10}$-alkyl, $C_1$–$C_{10}$-alkoxycarbonyl-$C_1$–$C_{10}$-alkyl, —N($R^9$)$R^{10}$, —SO$_2$N($R^{11}$)$R^{12}$, $C_1$–$C_4$-alkylene-SO$_2$N($R^{11}$)$R^{12}$, or —CON($R^{13}$)$R^{14}$, or (c) the second and third of $R^2$, $R^3$, and $R^4$ are attached to adjacent carbon atoms in the indicated benzene ring and, together with said adjacent carbon atoms, denote a carbocyclic group having 5 or 6 ring atoms or a heterocyclic group having 5 to 10 ring atoms, of which one or two are hetero atoms selected from nitrogen, oxygen, and sulfur, $R^9$ is hydrogen or $C_1$–$C_{10}$- and $R^{10}$ is hydrogen, $C_1$–$C_{10}$-alkyl, or —COR$^{15}$ where $R^{15}$ is $C_1$–$C_{10}$-alkyl, $C_1$–$C_{10}$-haloalkyl, $C_1$–$C_{10}$-alkoxy-$C_1$–$C_{10}$-alkyl, $C_1$–$C_{10}$-alkoxycarbonyl, carboxy-$C_1$–$C_{10}$-alkyl, or $C_1$–$C_{10}$-alkoxycarbonyl-$C_1$–$C_{10}$ alkyl, or $R^9$ and $R^{10}$ together with the nitrogen atom to which they are attached, denote a heterocyclic group having 5 or 6 ring atoms and one or two nitrogen atoms, or one nitrogen atom and one oxygen atom, in the ring, $R^{11}$ is hydrogen or $C_1$–$C_{10}$-alkyl and $R^{12}$ is hydrogen, $C_1$–$C_{10}$-, alkyl, hydroxy-$C_1$–$C_{10}$-alkyl, $C_1$–$C_{10}$-alkoxy-$C_1$–$C_{10}$-alkyl, carboxy-$C_1$–$C_{10}$-alkyl, or $C_1$–$C_{10}$-alkoxycarbonyl-$C_1$–$C_{10}$-alkyl, or $R^{11}$ and $R^{12}$ together with the nitrogen atom to which they are attached denote a heterocyclic group having 5 or 6 ring atoms and one or two nitrogen atoms, or one nitrogen atom and one oxygen atom, in the ring, and $R^{13}$ and $R^{14}$ are each independently hydrogen or $C_1$–$C_{10}$-alkyl.

6. A compound of claim 1 in which:

X is a group NR$^5$, $R^1$ is a $C_1$–$C_4$-alkyl, $C_2$–$C_4$-alkenyl, $C_3$–$C_5$ cycloalkyl, benzo-$C_5$–$C_6$-cycloalkyl, phenyl-$C_1$–$C_4$-alkyl, or $C_3$–$C_5$ cycloalkyl-$C_1$–$C_4$-alkyl group, which is optionally substituted by a hydroxy, carboxy or $C_1$–$C_4$-alkoxycarbonyl group, or $R^1$ is a heterocyclyl radical having 5 or 6 ring atoms and one or two nitrogen atoms, or one nitrogen atom and one oxygen atom, in the ring and optionally substituted on a ring nitrogen atom by $C_1$–$C_4$ alkyl, $C_1$–$C_4$-hydroxyalkyl, $C_1$–$C_4$-alkylcarbonyl, or phenyl-$C_1$–$C_4$-alkyl, or $R^1$ is a group of formula IV in which one of $R^6$, $R^7$, and $R^8$ is hydrogen, $C_1$–$C_4$-alkyl or alkoxy, and (i) the second and third of $R^6$, $R^7$, and $R^8$ are each independently hydrogen, $C_1$–$C_4$-alkyl or $C_1$–$C_4$-alkoxy or (ii) the second of $R^6$ $R^7$, and $R^8$ is hydrogen and the third of $R^6$, $R^7$ and $R^8$ is —N($R^9$)$R^{10}$, —SO$_2$N($R^{11}$)$R^{12}$ or —CON($R^{13}$)$R^{14}$, or (iii) the second and third of $R^6$, $R^7$, and $R^8$ are attached to adjacent carbon atoms in the indicated benzene ring and together with said adjacent carbon atoms denote a carbocyclic group having 5 or 6 ring atoms or a heterocyclic group having 5 or 6 ring atoms, of which one or two are nitrogen atoms, one of $R^2$, $R^3$, and $R^4$ is hydrogen, $C_1$–$C_4$-alkyl or $C_1$–$C_4$-alkoxy and (a) the second and third of $R^2$, $R^3$, and $R^4$ are each independently hydrogen, $C_1$–$C_4$-alkyl or $C_1$–$C_4$-alkoxy or (b) the second of $R^2$, $R^3$, and $R^4$ is hydrogen and the third of $R^2$, $R^3$, and $R^4$ is carboxy, $C_1$–$C_4$-alkoxycarbonyl, carboxy-$C_1$–$C_4$-alkyl, $C_1$–$C_4$-alkoxycarbonyl-$C_1$–$C_4$-alkyl, —N($R^9$)$R^{10}$, —SO$_2$N($R^{11}$)$R^{12}$, $C_1$–$C_4$-alkylene-SO$_2$N($R^{11}$)$R^{12}$, or —CON($R^{13}$)$R^{14}$, or (c) the second and third of $R^2$, $R^3$, and $R^4$ are attached to adjacent carbon atoms in the indicated benzene ring and denote, together with said adjacent carbon atoms, a heterocyclic group having 5 to 10 ring atoms, of which one or two are hetero atoms selected from nitrogen, oxygen and sulfur, $R^5$ is hydrogen or $C_1$–$C_4$-alkyl, $R^9$ is hydrogen or $C_1$–$C_4$ alkyl and $R^{10}$ is hydrogen, $C_1$–$C_4$ alkyl, or —COR$^{15}$ where $R^{15}$ is $C_1$–$C_4$-alkyl, $C_1$–$C_4$-haloalkyl, $C_1$–$C_4$-alkoxy, $C_1$–$C_4$-alkoxy-$C_1$–$C_4$ alkyl, $C_1$–$C_4$-alkoxycarbonyl, or $C_1$–$C_4$-alkoxycarbonyl-$C_1$–$C_4$-alkyl, or $R^9$ and $R^{10}$ together with the nitrogen atom to which they are attached denote a heterocyclic group having 5 or 6 ring atoms including one or two ring nitrogen atoms, or one nitrogen ring atom and one oxygen ring atom, $R^{11}$ is hydrogen or $C_1$–$C_4$-alkyl and $R^{12}$ is hydrogen, $C_1$–$C_4$-alkyl, hydroxy-$C_1$–$C_4$-alkyl, $C_1$–$C_4$-alkoxy-$C_1$–$C_4$-alkyl or $C_1$–$C_4$-alkoxycarbonyl- $C_1$–$C_4$-alkyl, or $R^{11}$ and $R^{12}$ together with the nitrogen atom to which they are attached denote a heterocyclic group having 5 or 6 ring atoms including one or two ring nitrogen atoms, or one nitrogen ring atom and one oxygen ring atom, and $R^{13}$ and $R^{14}$ are each independently hydrogen or $C_1$–$C_4$-alkyl.

7. A compound of claim 1, in which X is an oxygen atom, $R^1$ is $C_1$–$C_4$-alkyl, or $C_3$–$C_{10}$ cycloalkyl, one of $R^2$, $R^3$, and $R^4$ is hydrogen, and either (i) the second of $R^2$, $R^3$, and $R^4$ is hydrogen and the third of $R^2$, $R^3$, and $R^4$ is carboxy, $C_1$–$C_4$-alkoxycarbonyl or —N($R^9$)$R^{10}$ where $R^9$ and $R^{10}$ together with the attached nitrogen atom denote a heterocyclic group having 5 or 6 ring atoms including two ring nitrogen atoms or one ring nitrogen atom and one ring oxygen atom, or (ii) the second and third of $R^2$, $R^3$, and $R^4$ are attached to adjacent carbon atoms on the indicated benzene ring and together with the carbon atoms to which they are attached denote a heterocyclic group having 5 or 6 ring atoms, of which one or two are nitrogen atoms.

8. A compound of claim 1, in which X is a sulfur atom, $R^1$ is $C_1$–$C_4$-alkyl, two of $R^2$, $R^3$, and $R^4$ are hydrogen and the third of $R^2$, $R^3$, and $R^4$ is carboxy, $C_1$–$C_4$-alkoxycarbonyl, or —N($R^9$)$R^{10}$ where $R^9$ is hydrogen or $C_1$–$C_4$-alkyl and $R^{10}$ is —COR$^{15}$ where $R^{15}$ is $C_1$–$C_4$-alkyl, or $R^9$ and $R^{10}$ together with the nitrogen atom to which they are attached denote a heterocyclic group having 5 or 6 ring atoms including one or two ring nitrogen atoms or one ring nitrogen atom and one ring oxygen atom.

9. A compound for formula III

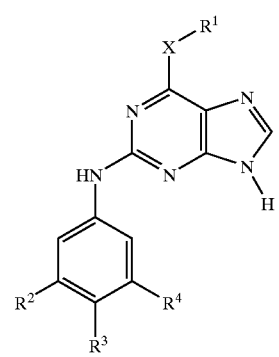

in free or pharmaceutically acceptable salt form, wherein (i) X is NH, $R^1$ is cyclopropyl, $R^2$ and $R^4$ are each hydrogen, and $R^3$ is NHCOOC(CH$_3$)$_3$; or (ii) X is NH, $R^1$ is cyclopropyl, $R^2$ and $R^4$ are each hydrogen, and $R^3$ is morpholino; or (iii) X is NH, $R^1$ is cyclobutyl, $R^2$ and $R^4$ are each hydrogen, and $R^3$ is 4-tert-butoxycarbonyl-1-piperazinyl; or (iv) X is NH, $R^1$ is cyclobutyl, $R^2$ and $R^4$ are each hydrogen, and $R^3$ is —N(CH$_3$)COCH$_3$; or (v) X is NH, $R^1$ is isopropyl, $R^2$ and $R^4$ are each hydrogen, and $R^3$ is —SO$_2$N(CH$_3$)$_2$; or (vi) X is NH, $R^1$ is cyclopropyl, $R^2$ and $R^4$ are each hydrogen, and $R^3$ is 4-acetyl-1-piperazinyl; or (vii) X is NH, $R^1$ is tert-butyl, $R^2$ is hydrogen, and $R^3$ and $R^4$ together denote —CH$_2$—O—CO—; or (viii) X is O, $R^1$ is cyclobutyl, $R^2$ and $R^4$ are each hydrogen, and $R^3$ is —N(CH$_3$)COCH$_3$; or (ix) X is NH, $R^1$ is cyclopropyl, $R^2$ and $R^4$ are each hydrogen, and $R^3$ is 4-methyl-1-piperazinyl; or (x) X is NH, $R^1$ is tert-butyl, $R^2$ and $R^4$ are each hydrogen, and $R^3$ is —N(CH$_3$)COCH$_3$; or (xi) X is NH, $R^1$ is isopropyl, $R^2$ and $R^4$ are each hydrogen, and $R^3$ is —N(CH$_2$CH$_3$)COCH$_3$; or (xii) X is NH, $R^1$ is cyclopropyl, $R^2$ and $R^4$ are each hydrogen, and $R^3$ is —N(CH$_3$)COCH$_2$CH$_3$.

10. A pharmaceutical composition comprising a compound of claim 1 together with a pharmaceutically acceptable diluent or carrier therefor.

11. A process for the preparation of compounds of claims 1 and their salts which comprises A) reacting a compound of formula

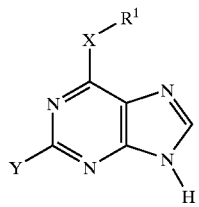

V with a compound of formula

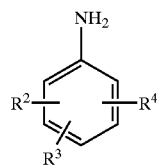

VI where X, $R^1$, $R^2$, $R^3$, and $R^4$ are as defined in claim 1 and Y is a leaving group, a free functional group in the compounds of formulae V and VI other that those involved in the reaction being protected, if necessary, by a removable protecting group; or (B) for the preparation of a compound of formula I where $R^2$, $R^3$, or $R^4$ is a carboxy or carboxyalkyl group, cleaving a corresponding compound of formula I in which $R^2$, $R^3$ or $R^4$ is an alkoxycarbonyl or alkoxycarbonylalkyl group respectively; or (C) for the preparation of a compound of formula I where $R^2$, $R^3$, or $R^4$ is an alkoxycarbonyl or alkoxycarbonylalkyl group, appropriately esterifying a corresponding compound of formula I in which $R^2$, $R^3$, or $R^4$ is a carboxy or carboxyalkyl group; or (D) for the preparation of a compound of formula I where $R^2$, $R^3$, or $R^4$ is a group of formula —SO$_2$N(R$^{11}$)R$^{12}$ as hereinbefore defined, appropriately aminating a corresponding compound of formula

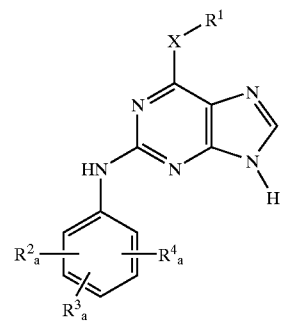

VII where $R^1$ is as hereinbefore defined and $R^2_a$, $R^3_a$, and $R^4_a$ are respectively the same as $R^2$, $R^3$, and $R^4$ as hereinbefore defined, with the exception that at least one of them is a group of formula —SO$_2$—Hal, where Hal is halogen; or (E) for the preparation of a compound of formula I where $R^2$, $R^3$, or $R^4$ is a group of formula —CON(R$^{13}$)R$^{14}$ as hereinbefore defined, appropriately aminating a corresponding compound of formula I where $R^2$, $R^3$, or $R^4$ is a carboxy group;

and optionally converting a resultant compound of formula I in protected form into a corresponding compound in unprotected form;

and recovering the resultant compound of formula I in free or salt form.

12. A method of treating an allergic condition, an inflammatory airways disease, or an obstructive airways disease which comprises administering to a patient in need of said treatment a therapeutically effective amount of a compound of claim 1.

* * * * *

UNITED STATES PATENT AND TRADEMARK OFFICE
CERTIFICATE OF CORRECTION

PATENT NO.   : 6,589,950 B1
DATED        : July 8, 2003
INVENTOR(S)  : Collingwood et al.

It is certified that error appears in the above-identified patent and that said Letters Patent is hereby corrected as shown below:

Column 46,
Line 46, should read:
-- $C_1$-$C_4$-alkyl group which is optionally substituted by a --.
Line 58, should read:
-- hydrogen and the third of $R^6$, $R^7$ and $R^8$ is carboxy, $C_1$-$C_{10}$- --.

Column 49,
Line 29, should read:
-- A process for the preparation of compounds of claim --.

Signed and Sealed this

Twenty-eighth Day of October, 2003

JAMES E. ROGAN
*Director of the United States Patent and Trademark Office*